United States Patent
Ma et al.

(10) Patent No.: US 12,370,162 B1
(45) Date of Patent: Jul. 29, 2025

(54) DIETARY GLYCINE AND SERINE RESTRICTION FOR CANCER TREATMENT

(71) Applicant: Rplushealth Limited, Grand Cayman (KY)

(72) Inventors: Xuelei Ma, Sichuan (CN); Chengyuan He, Sichuan (CN); Zhiwen Long, Sichuan (CN); Zhen Lei, Sichuan (CN)

(73) Assignee: Rplushealth Limited, Grand Cayman (KY)

( * ) Notice: Subject to any disclaimer, the term of this patent is extended or adjusted under 35 U.S.C. 154(b) by 0 days.

(21) Appl. No.: 19/008,588

(22) Filed: Jan. 2, 2025

(30) Foreign Application Priority Data

Nov. 25, 2024 (CN) .......................... 202411697055.2

(51) Int. Cl.
| | |
|---|---|
| *A61K 31/198* | (2006.01) |
| *A21D 2/24* | (2006.01) |
| *A21D 13/80* | (2017.01) |
| *A61K 39/395* | (2006.01) |
| *A61P 35/00* | (2006.01) |

(52) U.S. Cl.
CPC ............ *A61K 31/198* (2013.01); *A21D 2/245* (2013.01); *A21D 13/80* (2017.01); *A61K 39/3955* (2013.01); *A61P 35/00* (2018.01)

(58) Field of Classification Search
CPC .................................................. A61K 31/198
See application file for complete search history.

(56) References Cited

U.S. PATENT DOCUMENTS

2019/0008197 A1* 1/2019 Toyooka ............... A23L 33/135
2023/0346731 A1* 11/2023 Ma ........................ A61K 31/198

OTHER PUBLICATIONS

Li et al. MedComm, 2021, 2(1): 60-68.*
Tong, Huan et al., Dual impacts of serine/glycine-free diet in enhancing antitumor immunity and promoting evasion via PD-L1 lactylation, Cell Metabolism, vol. 36, Issue 12, Dec. 3, 2024, 2493-2510.e9.

* cited by examiner

*Primary Examiner* — Rei Tsang Shiao

(57) ABSTRACT

Provided is a food composition that comprises a plurality of amino acids or the salts thereof, wherein the plurality of amino acids or the salts thereof comprise about 0.0016-0.6 wt % of glycine or the salt thereof and about 0.00109-1.2 wt % of serine or the salt thereof. Also provided is a method for treating cancer in a subject in need thereof, comprising partly or completely substituting or replacing the normal diet of the subject with the food composition, and optionally administering to the subject a therapeutically effective amount of an anti-PD-1 antibody or an anti-PD-Li antibody.

18 Claims, 14 Drawing Sheets

DIETARY GLYCINE AND SERINE RESTRICTION FOR CANCER TREATMENT

INCORPORATION BY REFERENCE

All documents cited or referenced herein (including without limitation all literature documents, patents, published patent applications cited herein) ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference. Any Genbank sequences mentioned in this disclosure are incorporated by reference with the Genbank sequence to be that of the earliest effective filing date of this disclosure.

FIELD OF THE INVENTION

The disclosure provides a food composition that may comprise a plurality of amino acids, wherein the plurality of amino acids contains about 0.0016-0.6 wt % of glycine and about 0.00109-1.2 wt % of serine. In the disclosure, wt % indicates weight percentage. This food composition may be used as a meal replacement, especially a complete meal replacement, for tumor patients. Also provided is a method for treating cancer in a subject in need thereof, comprising controlling the subject's glycine and serine intake, such that the glycine and serine the subject takes into the body account for about 0.0016-0.6 wt % and about 0.00109-1.2 wt %, respectively, of the total amino acids the subject takes into the body.

BACKGROUND OF THE INVENTION

Cancer is a disease where cells grow uncontrollably and spread to other parts of the body. The proliferation and survival of cancer cells rely on rapid and selective biosynthesis of proteins, nucleotides and lipids. Serine and glycine are two non-essential amino acids that play important roles in such biosynthesis. They are also key to generation of antioxidant defense (Tajan M, et al., (2021) Serine synthesis pathway inhibition cooperates with dietary serine and glycine limitation for cancer therapy. *Nat Commun.* 12(1):366).

Cancer cells require sufficient amounts of glycine and serine. They may upregulate aerobic glycolysis, converting 3-phosphoglycerate (3-PG) into serine, as catalyzed by PHGDH, PSAT1 and PSPH. The de novo-synthesized serine may be later converted into glycine by SHMT1/2. Inhibition of PHGDH, and therefore the de novo synthesis of serine and glycine, has been shown to impair e.g., breast cancer cell proliferation, and the increased PHGDH expression was found to correlate with poor prognosis in e.g., breast, lung and gastric cancers (Geeraerts S L, et al., (2021) The ins and outs of serine and glycine metabolism in cancer. *Nat Metab.* 3(2):131-141).

Cancer cells may also rely on exogenous serine and glycine from the environment, for optimal growth (Yang, M., Vousden, K. (2016) Serine and one-carbon metabolism in cancer. *Nat Rev Cancer* 16: 650-662). The nutrients in the tumor environment may be manipulated, to impede cancer development. For example, the inhibitory effect of dietary serine and glycine restriction on tumor development has been confirmed in mice. The glycine- and serine-free diet had no negative health impacts on the mice, reduced tumor growth, and increased mouse survival (Maddocks, et al., (2017) Modulating the therapeutic response of tumours to dietary serine and glycine starvation. *Nature* 544: 372-376). Such a diet, when provided to people, would be consisted of protein-free or low-protein foods and amino acid shakes. Alternatively, tumor patients may take meal replacements, e.g., complete meal replacements, devoid of glycine and serine.

However, the deprivation of glycine and serine may have unintended negative effects. For example, tumor cells might adapt to such extreme conditions or initiate alternative metabolic pathways. The removal of these two amino acids from the food may also adversely affect the non-tumor cells, as serine and glycine are involved in metabolic pathways of normal cells.

Citation or identification of any document in this application is not an admission that such document is available as prior art to the present invention.

SUMMARY OF THE INVENTION

The inventors of the present application surprisingly found that, cancer cells, when cultured in medium without any glycine or serine, showed a relatively high migration activity, in spite of a low growth or proliferation rate. Cancer cell migration decreased when the glycine and serine levels in the medium increased, but cell growth or proliferation was enhanced to some extent. Therefore, to keep the cancer cells in an environment with appropriate glycine and serine levels may be the best way to control tumor development. Feeding tumor-bearing mice with feed having a glycine-to-total amino acid ratio in the range of 0.0016-0.6 wt % and a serine-to-total amino acid ratio in the range of 0.00109-1.2 wt % did result in tumor growth suppression. The other non-essential amino acids in the tumor environment showed less significant or even little effect on tumor growth or metastasis in vitro.

The inventors of the disclosure also found that a glycine- and serine-free diet increased PD-L1 molecules on tumor cell surfaces by promoting PD-L1 lactylation (data not shown). When a diet with a glycine-to-total amino acid ratio of 0.0016-0.6 wt % and a serine-to-total amino acid ratio of 0.00109-1.2 wt % was provided to tumor-bearing mice, such dietary restriction synergized with the anti-PD-1 therapy, which alone had minimal effect on e.g., pMMR/MSS colorectal cancer size. In later clinical trials, tumor size reduction was observed in tumor patients receiving the same dietary glycine and serine restriction with anti-PD-1 therapy.

Further, the dietary glycine and serine restriction alone has been found to promote growth, proliferation and survival of some immune cells, including $CD4^+$ T cells and $CD8^+$ T cells, and decrease regulatory T cells (Tregs), in e.g., tumor microenvironment.

Therefore, in a first aspect, the disclosure provides a composition that may comprise a plurality of amino acids or the salts thereof, wherein the plurality of amino acids or the salts thereof may comprise about 0.0016-0.6 wt % of glycine or the salt thereof and about 0.00109-1.2 wt % of serine or the salt thereof.

The composition may be a food composition.

The plurality of amino acids or the salts thereof may comprise about 0.0016 wt % or more, 0.2 wt % or more, or 0.4 wt % or more of glycine or the salt thereof. The plurality of amino acids or the salts thereof may comprise about 0.6 wt % or less, or 0.4 wt % or less of glycine or the salt thereof. In certain embodiments, the plurality of amino acids or the salts thereof may comprise about 0.2-0.6 wt % of glycine or the salt thereof. In certain embodiments, the plurality of amino acids or the salts thereof may comprise about 0.41 wt % of glycine or the salt thereof. In certain embodiments, the plurality of amino acids or the salts thereof may comprise about 0.5 wt % of glycine or the salt thereof.

The plurality of amino acids or the salts thereof may comprise about 0.00109 wt % or more, 0.2 wt % or more, 0.5 wt % or more, or 0.8 wt % or more of serine or the salt thereof. The plurality of amino acids or the salts thereof may comprise about 1.2 wt % or less, or 0.8 wt % or less of serine or the salt thereof. In certain embodiments, the plurality of amino acids or the salts thereof may comprise about 0.2-1.2 wt % or 0.5-1.2 wt % of serine or the salt thereof. In certain embodiments, the plurality of amino acids or the salts thereof may comprise about 0.81 wt % of serine or the salt thereof. In certain embodiments, the plurality of amino acids or the salts thereof may comprise about 0.5 wt % of serine or the salt thereof.

The plurality of amino acids in the food composition may comprise essential amino acids and non-essential amino acids, or the salts thereof, each at an appropriate level, if required.

The plurality of amino acids in the food composition may comprise essential amino acids selected from the group consisting of histidine, isoleucine, leucine, lysine, methionine, phenylalanine, threonine, tryptophan, and valine, or the salts thereof, each at an appropriate level. In certain embodiments, the plurality of amino acids in the food composition may comprise substantially or most of the 9 essential amino acids or the salts thereof, e.g., 7 or more, or 8 or more of the 9 essential amino acids. In certain embodiments, the plurality of amino acids in the food composition may comprise all the essential amino acids or the salts thereof, i.e., the plurality of amino acids in the food composition may comprise all the 9 essential amino acids or the salts thereof.

The plurality of amino acids in the food composition may comprise one or more non-essential amino acids selected from the group consisting of alanine, arginine, aspartic acid, cysteine, glutamine, proline, tyrosine, asparagine, and glutamic acid, or the salts thereof, each at an appropriate level, if required.

The plurality of amino acids may comprise about 1-5 wt % histidine. The plurality of amino acids may comprise about 3-7 wt % isoleucine. The plurality of amino acids may comprise about 6-13 wt % leucine. The plurality of amino acids may comprise about 4-10 wt % lysine. The plurality of amino acids may comprise about 1-6 wt % methionine. The plurality of amino acids may comprise about 3-6 wt % phenylalanine. The plurality of amino acids may comprise about 2-7 wt % threonine. The plurality of amino acids may comprise about 0.5-4 wt % tryptophan. The plurality of amino acids may comprise about 3-7 wt % valine.

The plurality of amino acids may comprise about 3-7 wt % alanine. The plurality of amino acids may comprise about 3-8 wt % arginine. The plurality of amino acids may comprise about 5-14 wt % aspartic acid. The plurality of amino acids may comprise about 1-4 wt % cysteine. The plurality of amino acids may comprise about 5-20 wt % glutamine. The plurality of amino acids may comprise about 3-6 wt % proline. The plurality of amino acids may comprise about 2-5 wt % tyrosine. The plurality of amino acids may comprise about 2-6 wt % asparagine. The plurality of amino acids may comprise about 10-15 wt % glutamic acid.

In certain embodiments, the plurality of amino acids may comprise about 18.34 wt % glutamine, about 10.57 wt % leucine, about 9.30 wt % aspartic acid, about 8.59 wt % lysine, about 7.18 wt % arginine, about 5.24 wt % valine, about 4.36 wt % phenylalanine, about 6.21 wt % alanine, about 4.75 wt % proline, about 5.61 wt % isoleucine, about 4.41 wt % threonine, about 2.23 wt % histidine, about 3.98 wt % tyrosine, about 2.62 wt % methionine, about 2.58 wt % tryptophan, about 2.81 wt % cysteine, about 0.81 wt % serine, and about 0.41 wt % glycine.

In certain embodiments, the plurality of amino acids may comprise about 4.86 wt % glutamine, about 9.82 wt % leucine, about 10.02 wt % aspartic acid, about 5.1 wt % lysine, about 6.2 wt % arginine, about 6.1 wt % valine, about 4.2 wt % phenylalanine, about 4.8 wt % alanine, about 4.4 wt % proline, about 4.63 wt % isoleucine, about 4.5 wt % threonine, about 2.9 wt % histidine, about 3.0 wt % tyrosine, about 5.9 wt % methionine, about 3.5 wt % tryptophan, about 1.4 wt % cysteine, about 0.81 wt % serine, about 0.41 wt % glycine, about 12.85 wt % glutamic acid, and about 4.6 wt % asparagine.

In certain embodiments, the plurality of amino acids may comprise about 6.1 wt % glutamine, about 11.08 wt % leucine, about 12.9 wt % aspartic acid, about 4.35 wt % lysine, about 6.4 wt % valine, about 4.1 wt % phenylalanine, about 6.35 wt % alanine, about 4.8 wt % proline, about 5.6 wt % isoleucine, about 5.5 wt % threonine, about 2.87 wt % histidine, about 3.4 wt % tyrosine, about 4.8 wt % methionine, about 2.07 wt % tryptophan, about 1.47 wt % cysteine, about 0.5 wt % serine, about 0.5 wt % glycine, about 13.2 wt % glutamic acid, and about 4.01 wt % asparagine.

The plurality of amino acids in the food composition of the disclosure may be L-amino acids or D-amino acids. In certain embodiments, the plurality of amino acids in the food composition of the disclosure may be L-amino acids. The glycine contained in the food composition may be L-glycine. The serine contained in the food composition may be L-serine.

The food composition of the disclosure may be formulated to provide at least the recommended daily intake of essential amino acids (with the optional exception of methionine) based on average daily total protein or amino acid consumption.

The food composition may further comprise one or more macronutrients and/or micronutrients. In certain embodiments, the food composition may comprise carbohydrates, fiber and/or fats as the macronutrients. In certain embodiments, the food composition may comprise vitamins, and/or minerals, as the micronutrients.

In certain embodiments, the food composition may comprise about 15-35 wt % amino acids, about 30-70 wt % carbohydrates, and about 10-50 wt % fats. In certain embodiments, the food composition may comprise 12.4 wt % amino acids, 14 wt % fats, 34.6 wt % carbohydrates, and 5 wt % fibers.

The food composition may be in the form of a solid, or a beverage.

The food composition may be a meal replacement, e.g., a complete meal replacement. The food composition may be used to partly or completely substituting the normal diet of a subject.

The food composition may be not a naturally occurring food.

The food composition may be formulated to be administered from once to eight times daily. In certain embodiments, the food composition may be formulated to be administered from three times to six times daily.

The disclosure also provides a meal replacement, which may comprise the food composition of the disclosure. The meal replacement may be a complete meal replacement.

In a second aspect, the disclosure provides a pharmaceutical composition, which may comprise the food composition of the disclosure, and a pharmaceutically acceptable carrier.

The pharmaceutical composition may further comprise an anti-tumor agent.

In certain embodiments, the pharmaceutical composition may further comprise an anti-PD-1 antibody (such as an antagonistic anti-PD-1 antibody), or an anti-PD-L1 antibody (such as an antagonistic anti-PD-L1 antibody).

In a third aspect, the disclosure provides a method for treating cancer in a subject in need thereof, which may comprise controlling the subject's glycine and serine intake, wherein the glycine the subject takes may account for about 0.0016-0.6 wt % of the total amino acids the subject takes, and the serine the subject takes may account for about 0.00109-1.2 wt % of the total amino acids the subject takes.

The method may comprise administering to the subject the food composition of the disclosure.

The method may comprise partly or completely substituting or replacing the normal diet of the subject with the food composition of the disclosure. In certain embodiments, the method may comprise completely substituting or replacing the normal diet of the subject with the food composition of the disclosure.

The method may comprise partly or completely substituting or replacing the normal diet of the subject over a time period of at least 1 day, 2 days, 3 days, 4 days, 5 days, 6 days, 7 days, at least 2 weeks, 3 weeks, 4 weeks, 5 weeks, 6 weeks, 7 weeks, 8 weeks, 9 weeks, 10 weeks, 11 weeks, 12 weeks, or until a therapeutic endpoint is observed, e.g., tumor shrinkage is observed.

The method may further comprise administering the subject a therapeutically effective amount of an anti-PD-1 antibody (such as an antagonistic anti-PD-1 antibody), or an anti-PD-L1 antibody (such as an antagonistic anti-PD-L1 antibody).

The anti-PD-1 antibody may be nivolumab or pembrolizumab.

The anti-PD-L1 antibody may be atezolizumab, avelumab, or duvalumab.

The subject may be human.

The cancer may be a solid cancer, including, but not limited to, colorectal cancer (e.g., pMMR/MSS colorectal cancer), esophageal cancer and nasopharyngeal cancer. The cancer may be an advanced one.

The disclosure also provides the use of the food composition of the disclosure in treating cancer, or in preparation of a medicament for treating cancer.

In a fourth aspect, the disclosure provides a method for sensitizing tumor cells to an anti-PD-1 or anti-PD-L1 therapy in a subject in need thereof, which may comprise controlling the subject's glycine and serine intake, wherein the glycine the subject takes may account for about 0.0016-0.6 wt % of the total amino acids the subject takes, and the serine the subject takes may account for about 0.00109-1.2 wt % of the total amino acids the subject takes.

The method may comprise administering to the subject the food composition of the disclosure.

The method may comprise partly or completely substituting or replacing the normal diet of the subject with the food composition of the disclosure. In certain embodiments, the method may comprise completely substituting or replacing the normal diet of the subject with the food composition of the disclosure.

The method may comprise partly or completely substituting or replacing the normal diet of the subject over a time period of at least 1 day, 2 days, 3 days, 4 days, 5 days, 6 days, 7 days, at least 2 weeks, 3 weeks, 4 weeks, 5 weeks, 6 weeks, 7 weeks, 8 weeks, 9 weeks, 10 weeks, 11 weeks, 12 weeks, or until a therapeutic endpoint is observed, e.g., tumor cell is sensitized.

The method may be performed before the anti-PD-1 or anti-PD-L1 therapy. Alternatively, the method and the anti-PD-1 or anti-PD-L1 therapy may be performed concurrently.

The tumor cells may be not sensitive to the anti-PD-1 or anti-PD-L1 therapy before the subject's glycine and serine intake is controlled.

The tumor cells may be cells of a solid tumor, including, but not limited to, colorectal cancer (e.g., pMMR/MSS colorectal cancer), esophageal cancer and nasopharyngeal cancer. The tumor cells may be cells of an advanced solid tumor.

The disclosure also provides the use of the food composition of the disclosure in sensitizing tumor cells to an anti-PD-1 or anti-PD-L1 therapy, or in preparation of a medicament for sensitizing tumor cells to an anti-PD-1 or anti-PD-L1 therapy.

In a fifth aspect, the disclosure provides a pharmaceutical composition that may comprise i) a food composition that may comprise a plurality of amino acids (including essential amino acids and non-essential amino acids) or the salts thereof, wherein the plurality of amino acids or the salts thereof may comprise about 0-0.0015 wt % of glycine or the salt thereof and about 0-0.00108 wt % of serine or the salt thereof, and ii) an anti-PD-1 antibody (such as an antagonistic anti-PD-1 antibody), or an anti-PD-L1 antibody (such as an antagonistic anti-PD-L1 antibody).

The food composition and the components in the composition are defined as in the first aspect, except the glycine and serine levels.

The disclosure also provides a method for treating cancer in a subject in need thereof, which may comprise i) controlling the subject's glycine and serine intake, wherein the glycine the subject takes may account for about 0-0.0015 wt % of the total amino acids the subject takes, and the serine the subject takes may account for about 0-0.00108 wt % of the total amino acids the subject takes, and ii) administering the subject a therapeutically effective amount of an anti-PD-1 antibody (such as an antagonistic anti-PD-1 antibody), or an anti-PD-L1 antibody (such as an antagonistic anti-PD-L1 antibody). The method may comprise partly or completely substituting or replacing the normal diet of the subject with a food composition, wherein the amino acids or the salts thereof in the food composition may comprise about 0-0.0015 wt % of glycine or the salt thereof and about 0-0.00108 wt % of serine or the salt thereof.

The disclosure further provides a method for sensitizing tumor cells to an anti-PD-1 or anti-PD-L1 therapy in a subject in need thereof, comprising controlling the subject's glycine and serine intake, wherein the glycine the subject takes may account for about 0-0.0015 wt % of the total amino acids the subject takes, and the serine the subject takes may account for about 0-0.00108 wt % of the total amino acids the subject takes. In certain embodiments, the method may comprise partly or completely substituting or replacing the normal diet of the subject with a food composition, wherein the amino acids or the salts thereof in the food composition may comprise about 0-0.0015 wt % of glycine or the salt thereof and about 0-0.00108 wt % of serine or the salt thereof.

The method is defined as in the third and fourth aspects, except the glycine and serine levels in the food composition.

Other features and advantages of the instant disclosure will be apparent from the following detailed description and examples, which should not be construed as limiting. The contents of all references, Genbank entries, patents and published patent applications cited throughout this application are expressly incorporated herein by reference.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

DESCRIPTION OF THE DRAWINGS

The following detailed description, given by way of example, but not intended to limit the invention solely to the specific embodiments described, may best be understood in conjunction with the accompanying drawings.

DETAILED DESCRIPTION OF THE INVENTION

Figure 1:
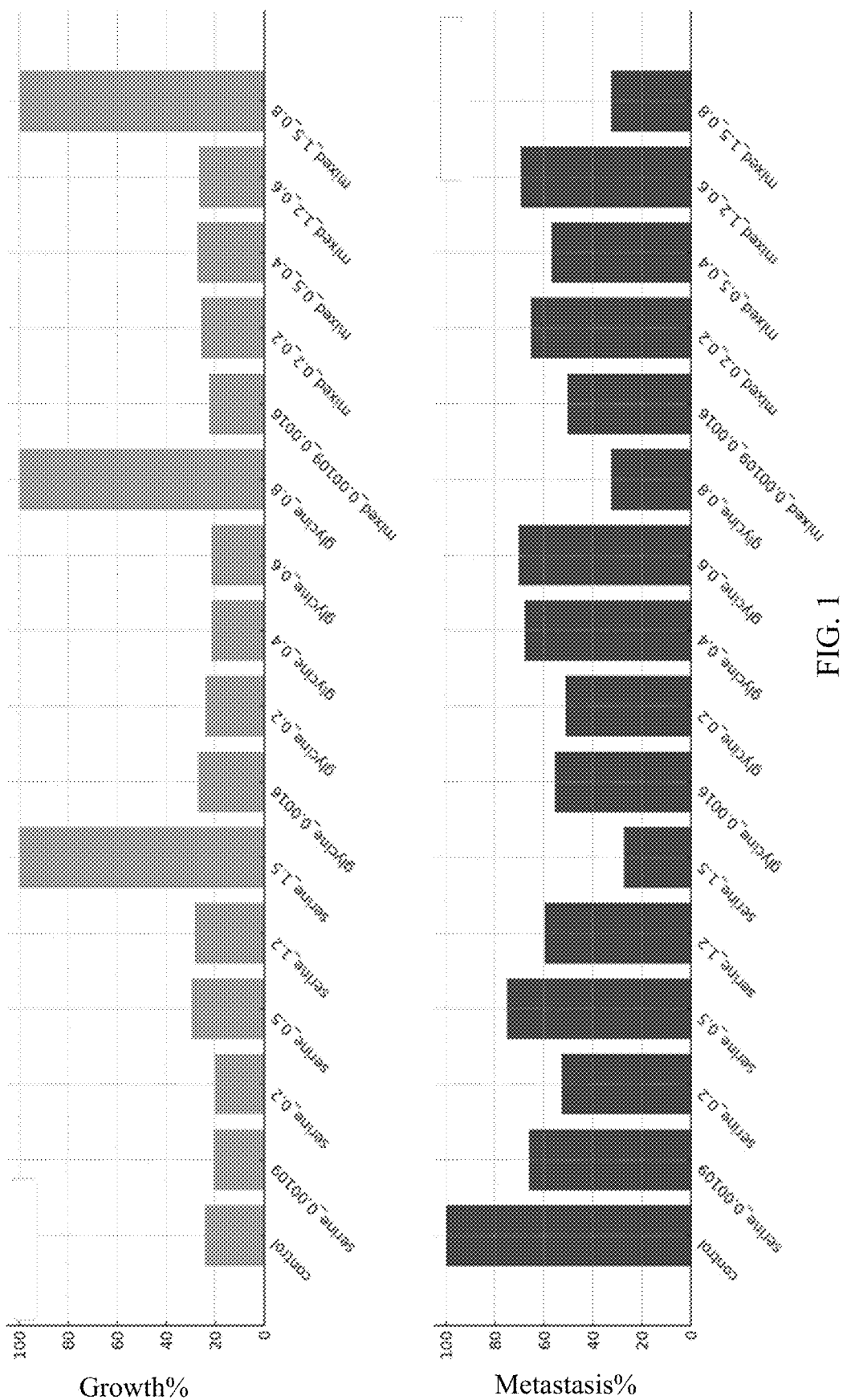
FIG. 1 shows the cell growth % (top panel) and metastasis % (bottom panel) of A431 cells cultured in absence of or in presence of glycine and serine at different concentrations.
Figure 2:
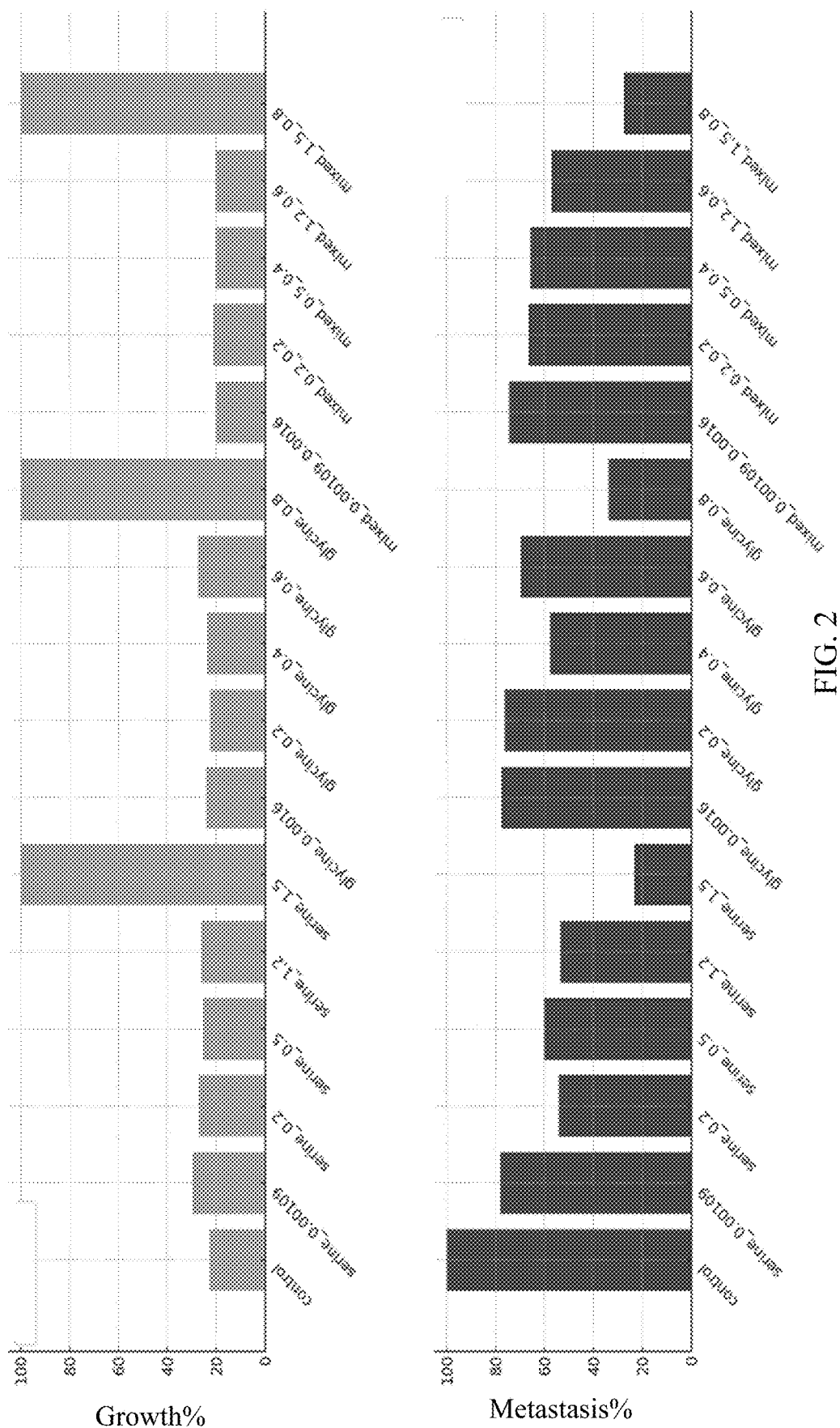
FIG. 2 shows the cell growth % (top panel) and metastasis % (bottom panel) of MCF-7 cells cultured in absence of or in presence of glycine and serine at different concentrations.
Figure 3:
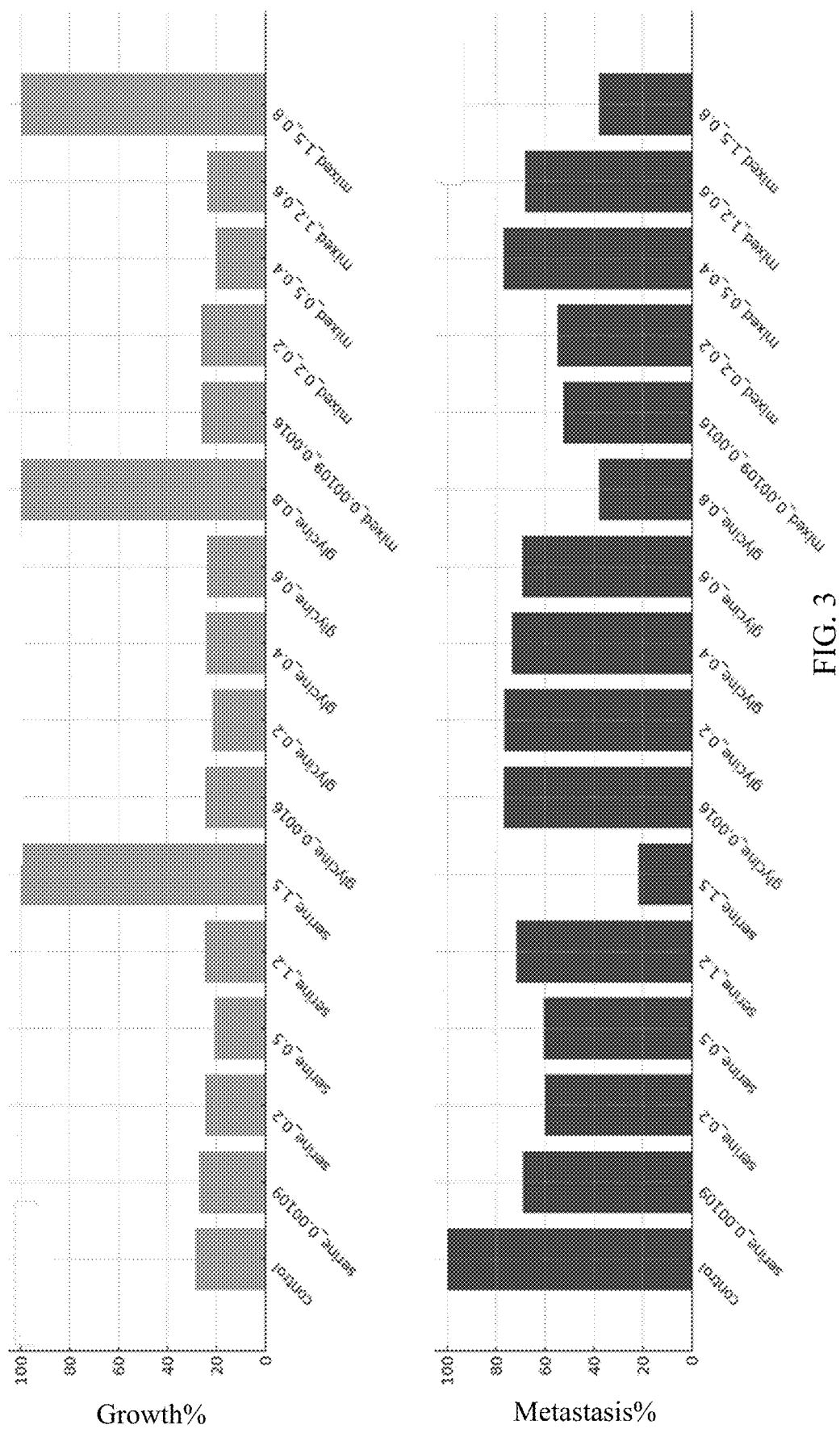
FIG. 3 shows the cell growth % (top panel) and metastasis % (bottom panel) of HeLa cells cultured in absence of or in presence of glycine and serine at different concentrations.
Figure 4:
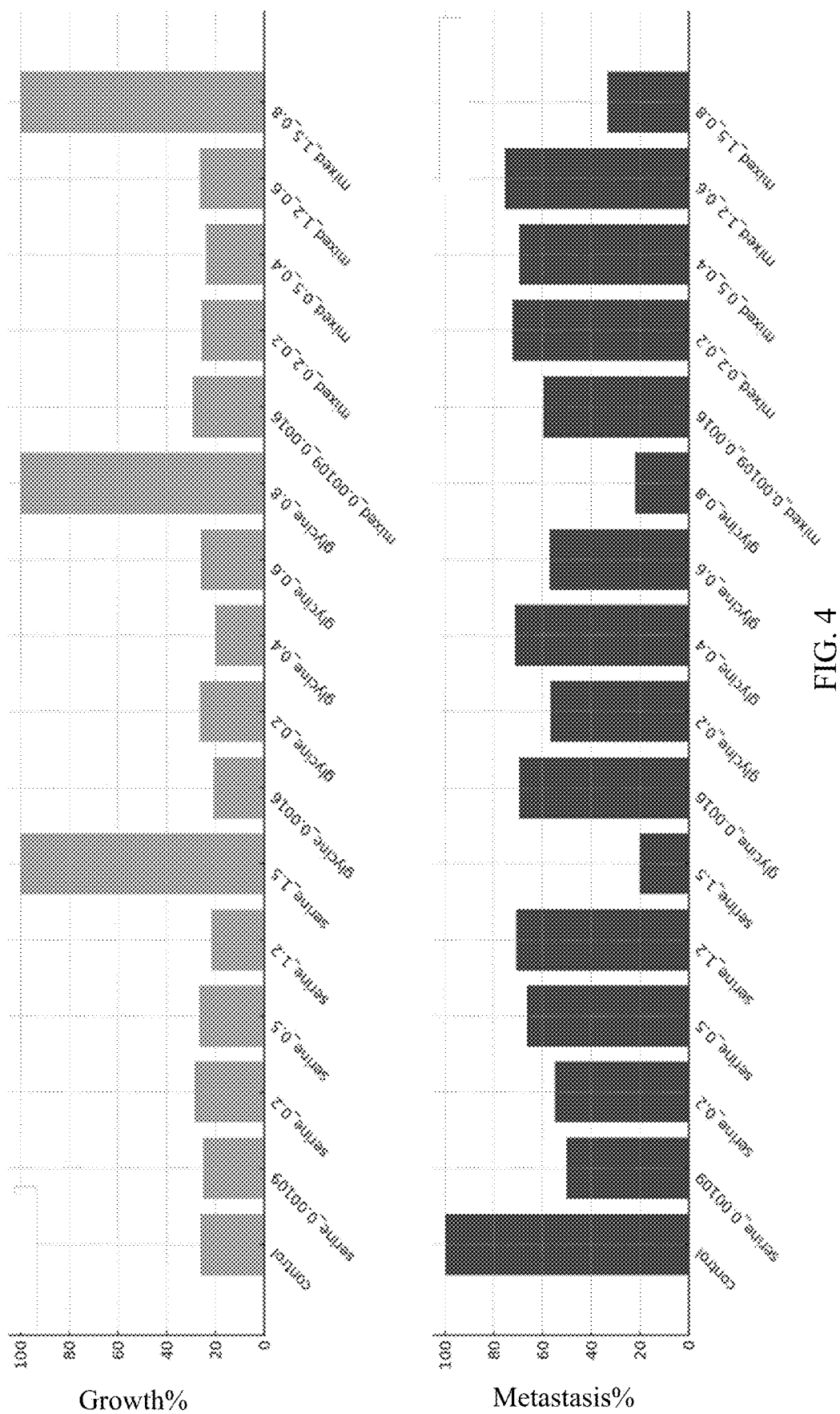
FIG. 4 shows the cell growth % (top panel) and metastasis % (bottom panel) of HepG2 cells cultured in absence of or in presence of glycine and serine at different concentrations.
Figure 5:
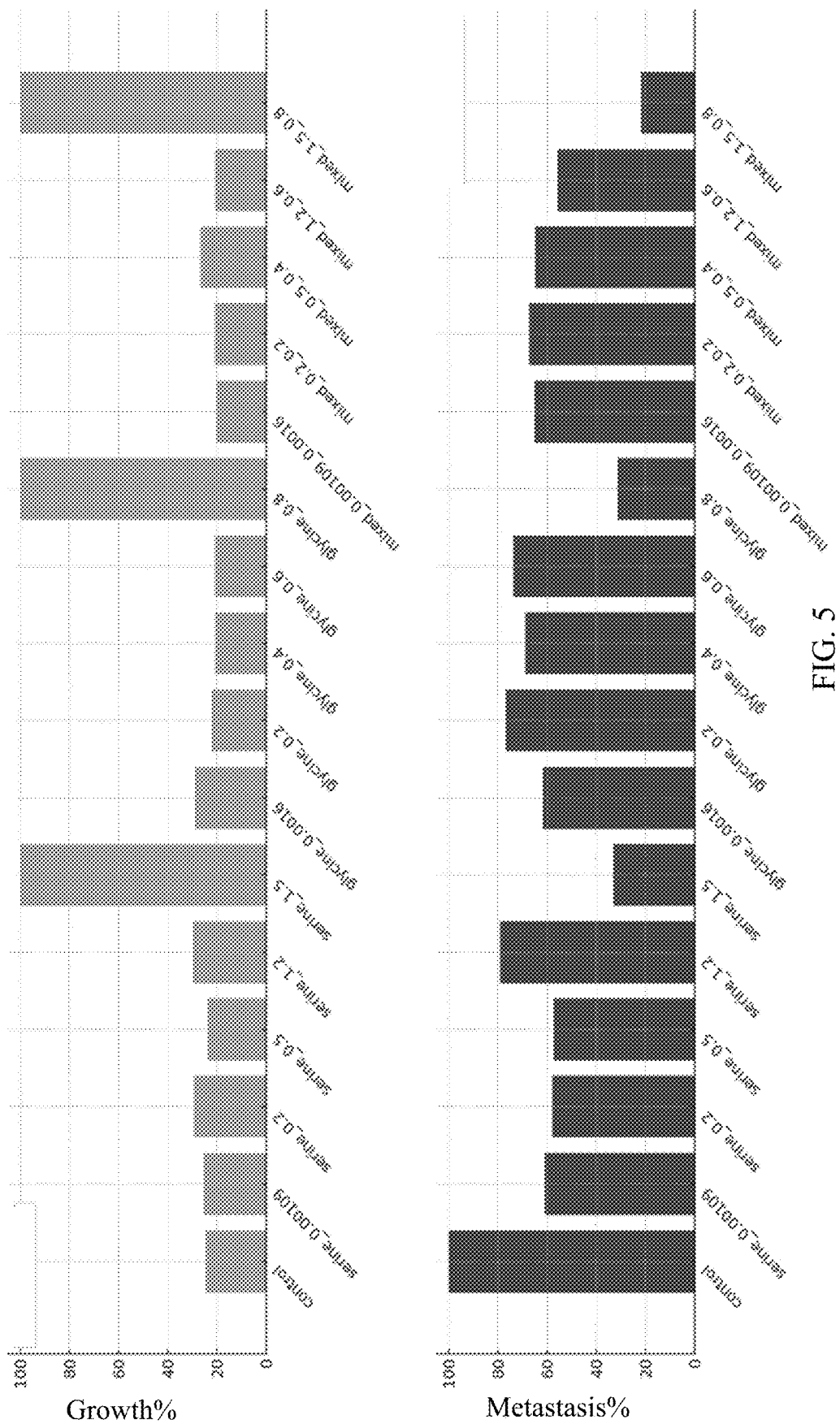
FIG. 5 shows the cell growth % (top panel) and metastasis % (bottom panel) of PC3 cells cultured in absence of or in presence of glycine and serine at different concentrations.
Figure 6:
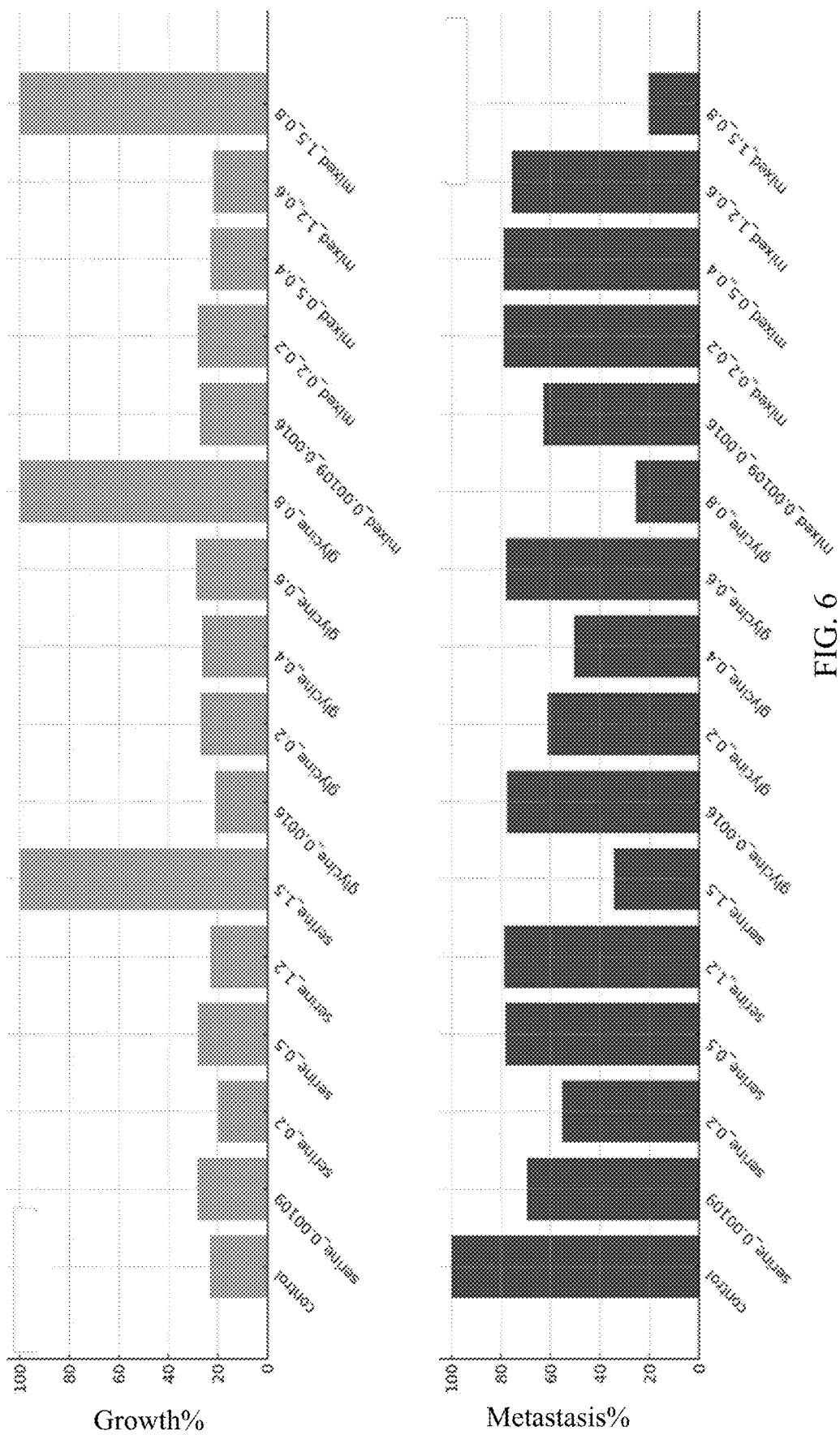
FIG. 6 shows the cell growth % (top panel) and metastasis % (bottom panel) of SKOV3 cells cultured in absence of or in presence of glycine and serine at different concentrations.
Figure 7:
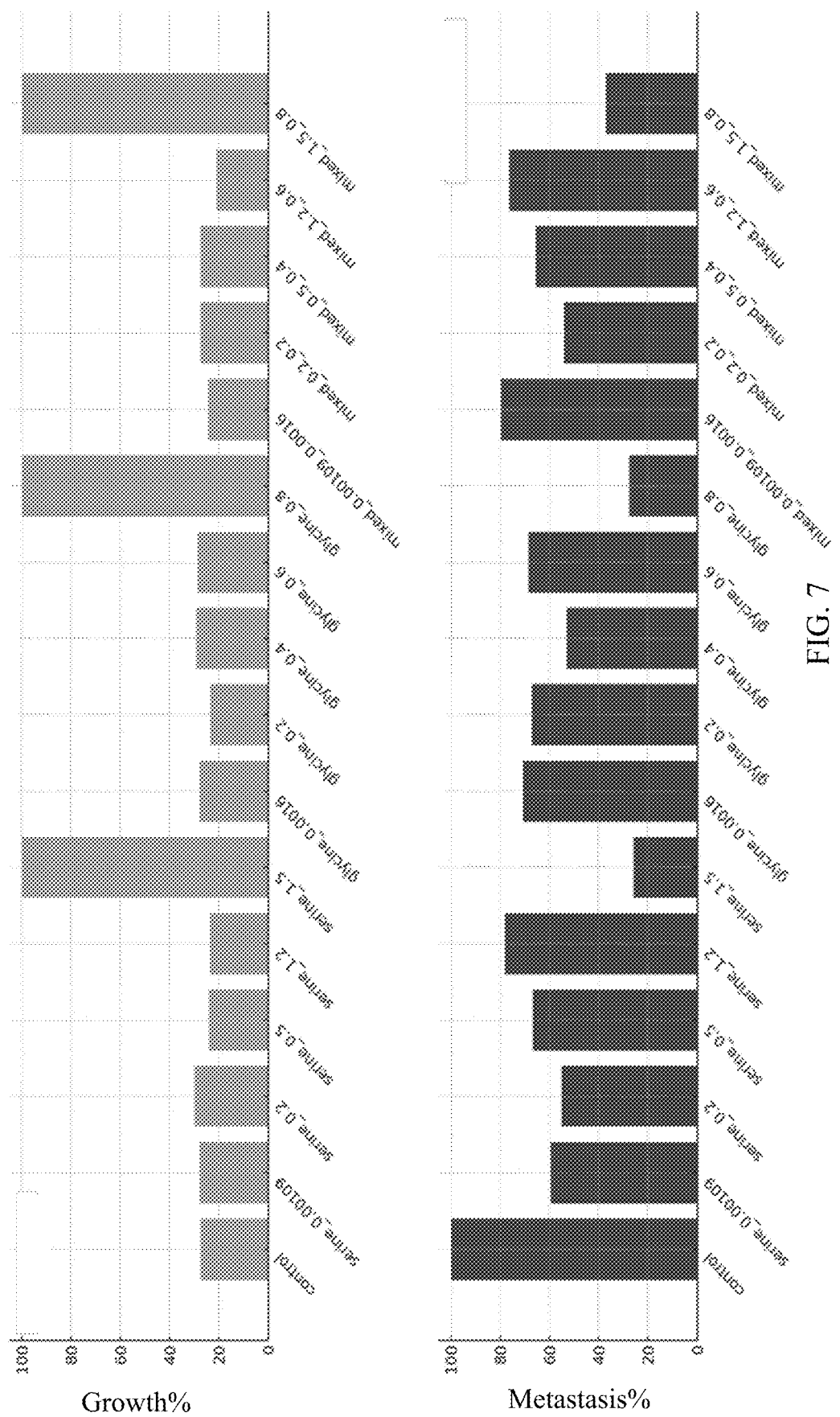
FIG. 7 shows the cell growth % (top panel) and metastasis % (bottom panel) of A549 cells cultured in absence of or in presence of glycine and serine at different concentrations.
Figure 8:
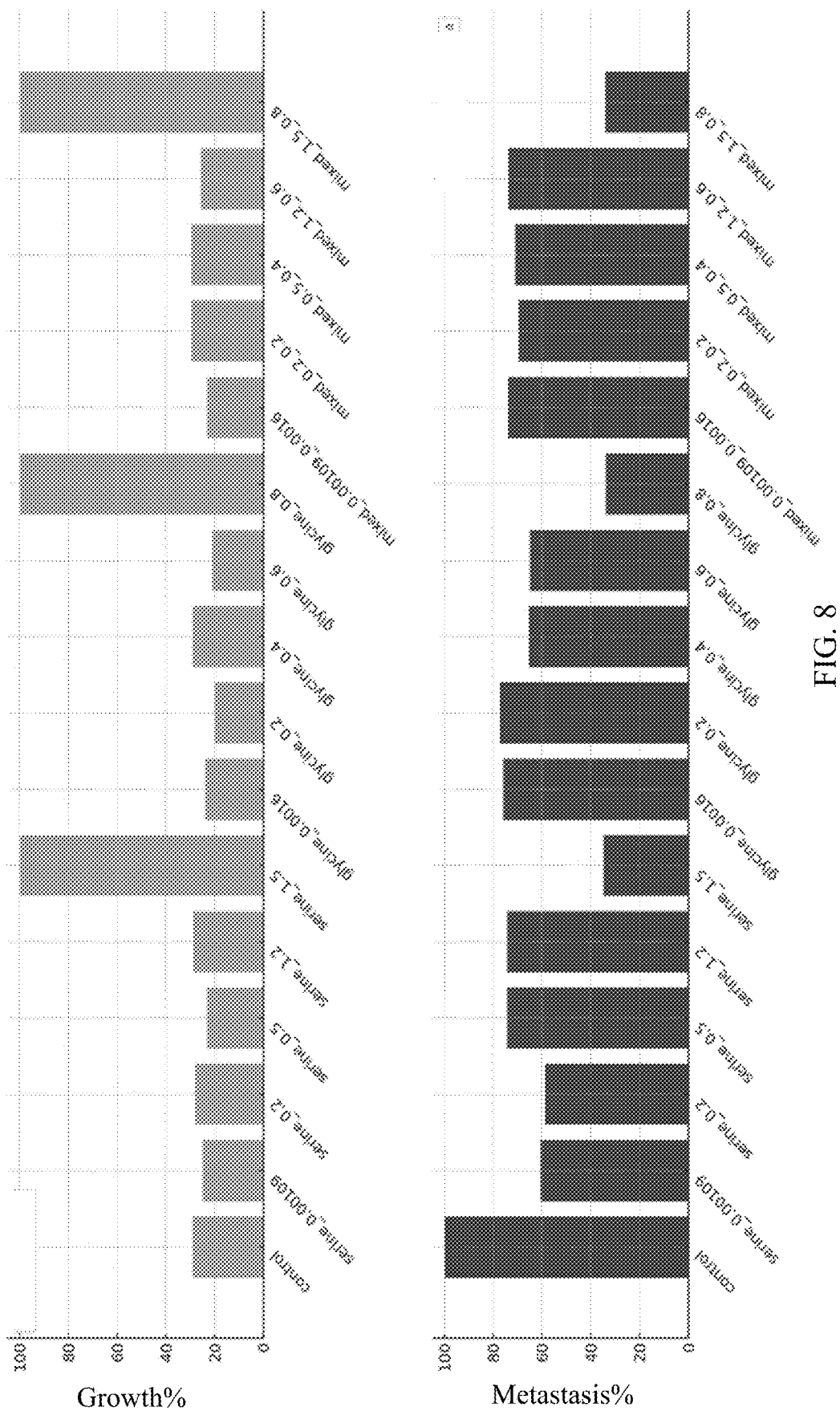
FIG. 8 shows the cell growth % (top panel) and metastasis % (bottom panel) of U251 cells cultured in absence of or in presence of glycine and serine at different concentrations.
Figure 9:
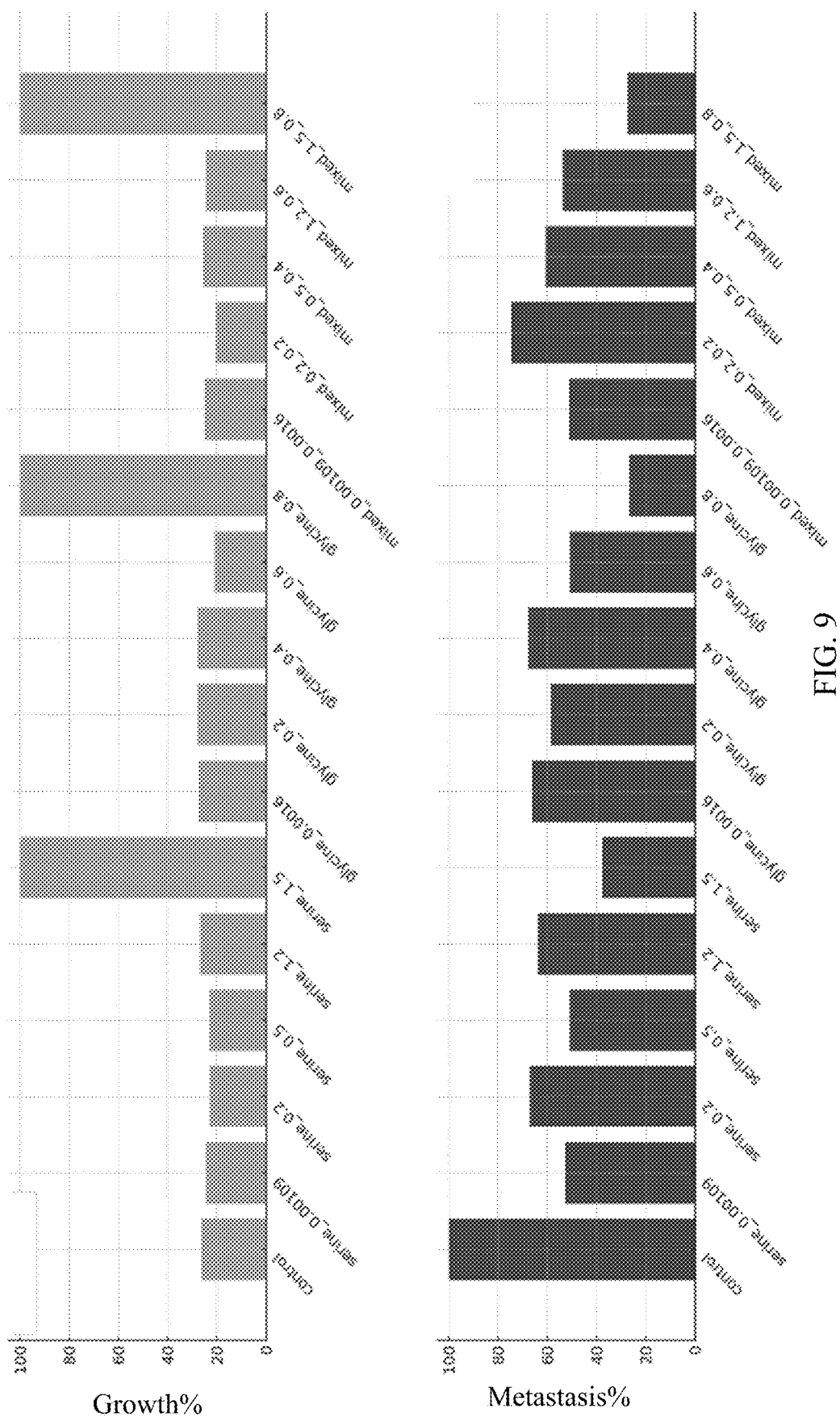
FIG. 9 shows the cell growth % (top panel) and metastasis % (bottom panel) of K562 cells cultured in absence of or in presence of glycine and serine at different concentrations.
Figure 10:
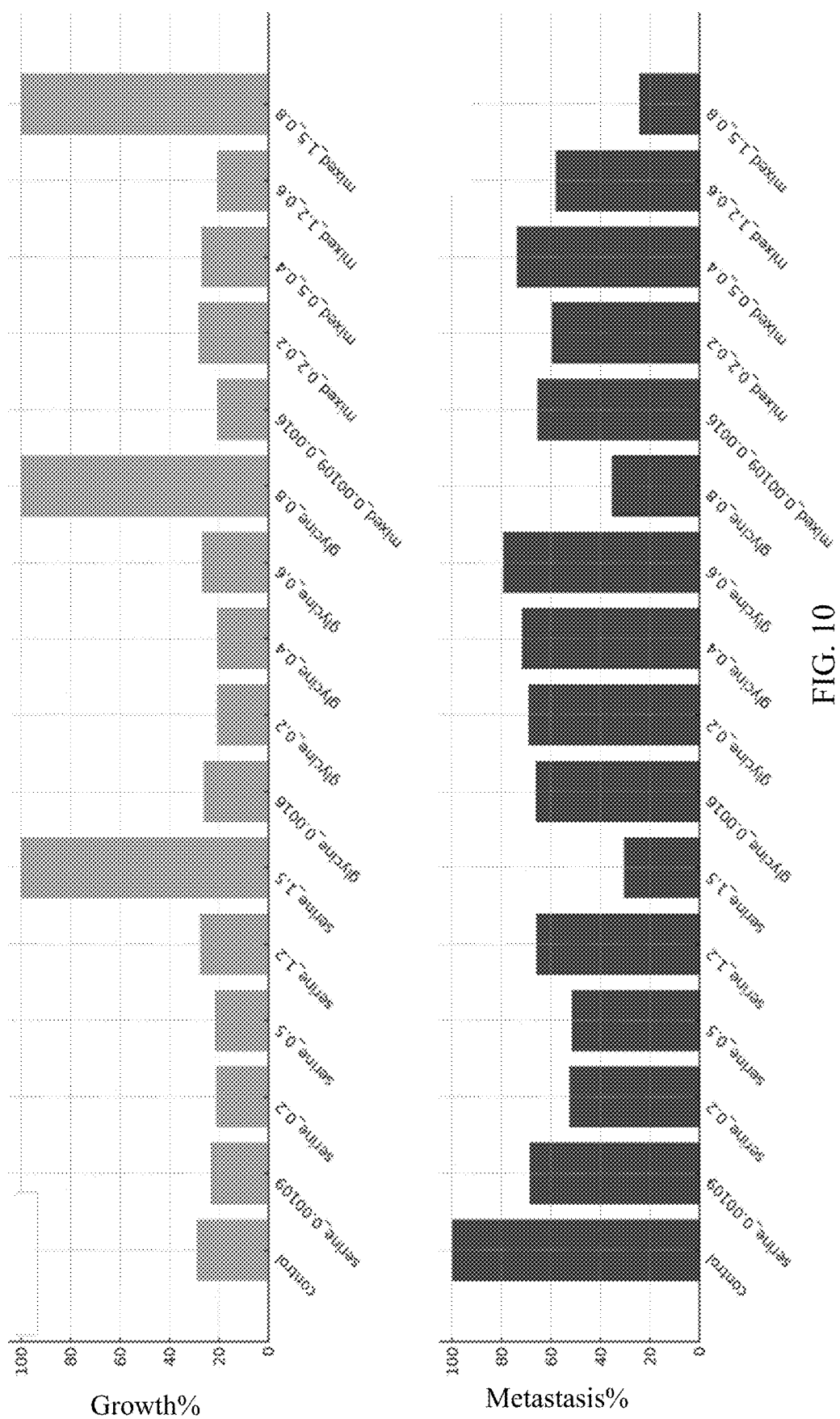
FIG. 10 shows the cell growth % (top panel) and metastasis % (bottom panel) of Caco-2 cells cultured in absence of or in presence of glycine and serine at different concentrations.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, it will be understood that modifications and variations are encompassed within the spirit and scope of the instant disclosure.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

The term "about" or "approximately" means within an acceptable error range for the particular value as determined by one of ordinary skill in the art, which will depend in part on how the value is measured or determined, i.e., the limitations of the measurement system. For example, "about" can mean within one or more than one standard deviation, per the practice in the art. Alternatively, "about" can mean a range of up to 20%, up to 15%, up to 10%, up to 5%, or up to 1% of a given value.

The "essential amino acids" are 9 amino acids that cannot be synthesized in the body and must be obtained from the daily diet, including histidine, isoleucine, leucine, lysine, methionine, phenylalanine, threonine, tryptophan and valine; while the "non-essential amino acids" are those that can be synthesized in the body, including alanine, arginine, asparagine, aspartic acid, cysteine, glutamic acid, glutamine, glycine, proline, serine, and tyrosine.

A "normal diet" or "regular diet" refers to a diet that usually combines a variety of foods, including grains, vegetables, fruits, dairy products, meat and fish, and does not require any dietary modification or intervention.

The term "dietary serine and glycine restriction" herein refers to a dietary intervention that reduces serine and glycine intake, as compared to normal diet where usually natural occurring proteins are consumed which contain serine and glycine at relatively high levels. The term "serine and glycine deprivation" or "dietary serine and glycine deprivation" refers to a dietary intervention that inhibits serine and glycine intake.

The "meal replacement" refers to a convenient and nutritionally balanced alternative to a traditional meal, typically available in the form of powders, ready-to-drink meals, or bars. A complete meal replacement or a full-day replacement is designed to replace or substitute all meals in a day, including breakfast, lunch, supper, and between-meal snacks.

The term "sensitize" or "sensitizing" means to cause someone or something to respond to certain stimuli that he/she or it may be not responsive to. For example, to "sensitive" cells to anti-PD-1 therapy means to make the cells which may be not responsive to anti-PD-1, to respond to such therapy.

The term "macronutrients" refer to the nutrients that the body needs in large amounts, which include fats, carbohydrates, proteins and fibers.

The term "micronutrients" refer to the elements required by the body in small quantities, including vitamins and minerals. Examples of micronutrients include iron, cobalt, chromium, iodine, copper, zinc, molybdenum, vitamin C, and Vitamin D.

The term "subject" includes any human or nonhuman animal. The term "nonhuman animal" includes all vertebrates, e.g., mammals and non-mammals, such as non-human primates, sheep, dogs, cats, cows, horses, chickens, amphibians, and reptiles, although mammals are preferred, such as non-human primates, sheep, dogs, cats, cows and horses.

The term "therapeutically effective amount" means an amount of a molecule, or a composition, that is sufficient to prevent or ameliorate the symptoms associated with a disease or condition (such as tumor) and/or lessen the severity of the disease or condition. A therapeutically effective amount is understood to be in context of the condition being treated, where the actual effective amount is readily discerned by those of skill in the art.

As used herein, the term "treatment/treating" refers to a method that is carried out to obtain a beneficial or desired clinical outcome. For the purpose of the disclosure, the beneficial or desired clinical outcome includes, but not limited to, easing symptom, narrowing the scope of disease, stabilizing (i.e., not aggravating) the state of disease, delaying or slowing the progress of disease, and alleviating symptoms (either partially or completely), no matter detectable or not detectable. In addition, "treatment" also results in a prolonged survival period compared to the expected survival period (if no treatment is accepted). The beneficial or desired clinical outcome described herein may include, but not limited to, slowing of tumor progression, cancer regression, enhancement of anti-tumor immune response, a reduction in tumor growth or size, necrosis of the tumor, a decrease in severity of at least one disease symptom, an increase in frequency and duration of disease symptom-free periods, a prevention of impairment or disability due to the disease affliction, or otherwise amelioration of disease symptoms in the patient.

A "pharmaceutically acceptable carrier" means a carrier that is useful in preparing a pharmaceutical composition that is generally safe, non-toxic and neither biologically nor otherwise undesirable, and includes a carrier that is acceptable for veterinary use as well as human pharmaceutical use. Pharmaceutically acceptable carriers include diluents (fillers, bulking agents, e.g. lactose, microcrystalline cellulose), disintegrants (e.g. sodium starch glycolate, croscarmellose sodium), binders (e.g. PVP, HPMC), lubricants (e.g. magnesium stearate), glidants (e.g. colloidal $SiO_2$), solvents/co-solvents (e.g. aqueous vehicle, Propylene glycol, glycerol), buffering agents (e.g. citrate, gluconates, lactates), preservatives (e.g. Na benzoate, parabens (Me, Pr and Bu), BKC), anti-oxidants (e.g. BHT, BHA, Ascorbic acid), wetting agents (e.g. polysorbates, sorbitan esters), thickening agents (e.g. methylcellulose or hydroxyethylcellulose), sweetening agents (e.g. sorbitol, saccharin, aspartame, acesulfame), flavoring agents (e.g. peppermint, lemon oils, butterscotch, etc.), and humectants (e.g. propylene, glycol, glycerol, sorbitol).

Amino acids are the building blocks of protein, and required for cell survival and proliferation. The amino acids serve many important purposes, including providing energy to boost the immune responses, aiding tissue growth and repair, and helping with muscle function and development. Nine of these amino acids are essential ones and must be obtained from the daily diet. Generally, the proteins as consumed are digested and broken down into amino acids. The non-essential ones can be produced within the body.

Cancer cells reprogram their metabolism to support unrestricted proliferation, and thus have higher demands for amino acids such as serine and glycine. They may upregulate aerobic glycolysis, converting 3-phosphoglycerate (3-PG) to serine, and then converting serine to glycine. They may also uptake serine and glycine from their surrounding environment, for optimal growth, proliferation and survival. Studies have shown dietary glycine and serine deprivation, i.e., completely removing glycine and serine from the food as consumed, may suppress tumor growth and increase lifespan in tumor-bearing mice.

The inventors of the present application cultured cancer cells in media with no glycine or serine, or with different glycine and serine concentrations, and found that, i) the cancer cells cultured with relatively high glycine and serine levels showed high growth or proliferation rate, and ii) the cancer cells cultured in medium without any glycine or serine showed the highest migration ability. Thus, the inventors came up with the conclusion that to keep the cancer cells in an environment with appropriate glycine and serine levels may be the best way to control tumor development.

With the discoveries above, the inventors of the disclosure designed a food composition with a glycine-to-total amino acid ratio in the range of 0.0016-0.6 wt % and a serine-to-total amino acid ratio in the range of 0.00109-1.2 wt %. As the food composition is intended to be used as a meal replacement, especially a complete meal replacement, and the total daily consumption amount is somewhat restricted, tumor patients taking the meal replacement may probably maintain glycine and serine in serum and/or tumor environment, at relatively low levels.

According to "Amino-acid content of foods and biological data on proteins" published by Food and Agriculture Organization (FAO) of the United Nations, and some review or research papers (e.g., Gorissen S H M, et al., (2018) Protein content and amino acid composition of commercially available plant-based protein isolates. *Amino Acids*. 50(12):1685-1695; Kang J S. (2020) Dietary restriction of amino acids for Cancer therapy. *Nutr Metab (Lond)*. 17:20), no naturally occurring food or protein has its glycine/serineto-total amino acids ratio at such a low level as in the food composition or meal replacement of the disclosure.

The use of such a food composition or meal replacement, can avoid extreme dietary restrictions, as occurred in the glycine-serine-free diet, which might disrupt the body's metabolism and potentially impair other physiological functions.

The food composition or meal replacement of the disclosure, when orally administered to animals or human beings, showed tumor suppression effects, as shown in Example 3 and Example 5 below, and particularly increased the proportion of $GZMB^+CD4^+$ T cells in $CD4^+$ cells and the proportion of $GZMB^+CD8^+$ T cells in $CD8^+$ cells in tumor patients, as shown in Example 5. In the inventors' other studies, the glycine and serine-free diet resulted in significant increase in the proportion of T cells with sharp rise of naive T cells and effector T cells, and a significant decrease in suppressive regulatory T cells (Tregs).

In another study of the inventors, a glycine- and serine-free diet was found to increase PD-L1 molecules on tumor cell surfaces by promoting PD-L1 lactylation. Lactylation of PD-L1 refers to a post-translational modification where lactate molecules attach to the PD-L1 protein. In tumor cells, hypoxic (low oxygen) environments lead to increased production of lactic acid. This lactic acid is taken up through monocarboxylate transporters (MCTs), and it can modify proteins, including PD-L1, through a process called lactylation. The glycine- and serine-free diet significantly increased PD-L1 protein levels in tumor cells without a corresponding rise in mRNA levels, indicating that the regulation occurs post-translationally. Further analysis revealed that hypoxic conditions promote lactylation of PD-L1, stabilizing the protein and preventing its degradation. That is, lactylation inhibits PD-L1 from being degraded through the lysosomal pathway, thereby maintaining higher levels of PD-L1 on the cell surface. The lactylation process was manipulated later using chemical agents. Increasing lactylation stabilized PD-L1, while inhibiting it led to faster degradation. These results provide strong evidence that lactylation plays a key role in regulating PD-L1 stability, which may contribute to the tumor's ability to evade immune responses.

In view of the above, the inventors of the disclosure combined the dietary glycine and serine restriction with the anti-PD-1 therapy in tumor treatment. It turned out that, both the glycine-serine-free diet, and the glycine-serine-low diet (with a glycine-to-total amino acid ratio of 0.0016-0.6 wt % and a serine-to-total amino acid ratio of 0.00109-1.2 wt %), synergized with the anti-PD-1 treatment, in suppression of colorectal cancer and esophageal cancer, as shown in e.g., Example 3 and Example 5 below, such as pMMR/MSS colorectal cancer. It is known in the art that the anti-PD-1 therapy alone showed minimal effect on pMMR/MSS colorectal cancer.

Therefore, the disclosure provides a food composition that may comprise a plurality of amino acids or the salts thereof, wherein the plurality of amino acids or the salts thereof may comprise about 0.0016-0.6 wt % of glycine or the salt thereof and about 0.00109-1.2 wt % of serine or the salt thereof.

As the food composition of the disclosure is designed to partly or completely substitute the normal diet of a tumor patient, the plurality of amino acids should comprise all (or substantially all) the essential amino acids, and optionally some non-essential amino acids. In certain embodiments, the plurality of amino acids in the food composition may comprise substantially or most of the 9 essential amino acids or the salts thereof, e.g., 7 or more, or 8 or more of the 9 essential amino acids. In certain embodiments, the plurality of amino acids in the food composition may comprise all the essential amino acids or the salts thereof, i.e., the plurality of amino acids in the food composition may comprise all the 9 essential amino acids or the salts thereof.

The amino acids present in the food composition of the disclosure may be amino acids in free form, in prodrug form, salts or amino acid esters. Amino acids with one or more N-terminal or C-terminal modification, and homopolymer, homodimer, heteropolymer and heterodimer forms may also be contemplated.

A food composition of the disclosure may be formulated to provide at least the recommended daily intake of essential amino acids based on average daily total protein consumption, unless otherwise stated herein. The recommended daily intake of essential amino acids by the Institute of Medicine, as based on average daily total protein consumption, is: histidine 18 mg/g protein; isoleucine 25 mg/g protein; leucine 55 mg/g protein; lysine 51 mg/g protein; methionine and cysteine combined 25 mg/g protein; phenylalanine and tyrosine combined 47 mg/g protein; threonine 27 mg/g protein; tryptophan 7 mg/g protein; and valine 32 mg/g protein.

The institute of medicine recommends that protein is consumed at a rate of 0.8 grams per kilogram per day of body weight for adults for example. The European Society for Palliative Care (ESPC) recommends a minimum protein intake of 1.0 g/kg body weight per day for cancer patients, to maintain or restore lean body mass. The food composition may be formulated to provide at least 0.8 or 1.0 grams protein per kg body weight during recommended daily consumption of the composition.

Also, as the food composition of the disclosure is designed to partly or completely substitute the normal diet of a tumor patient, it should contain one or more macronutrients (other than the proteins or amino acids), and/or micronutrients. The food composition may comprise carbohydrates, fiber and/or fats as the macronutrients. The food composition may comprise vitamins, and/or minerals, as the micronutrients.

Guidance on macronutrients and suggested recommended daily amounts may be found in the Dietary Reference Intakes for Energy, Carbohydrate, Fiber, Fat, Fatty Acids, cholesterol, protein and amino acids released by the Institute of Medicine September 2002. A non-exhaustive list of macronutrients which may be additional components of the food composition include: carbohydrates, fiber and fats (such as n-6 polyunsaturated fatty acids, n-3 polyunsaturated fatty acids, saturated and trans fatty acids and cholesterol).

A non-exhaustive list of micronutrients includes Vitamin A, Vitamin C, Vitamin D, Vitamin E, Vitamin K, Thiamin, Riboflavin, Niacin, Vitamin B6, folate, Vitamin B12, Pantothenic acid, biotin, choline, calcium, chromium, copper, fluoride, iodine, iron, magnesium, molybedenum, phosphorus, selenium, zinc, potassium, sodium, and chloride. Suitably the food composition may be formulated to provide these in acceptable or recommended daily intake amounts as detailed in the publication "Dietary Reference Intakes: RDA and AI for Vitamins and Elements", NAS. IOM. Food and Nutrition Board.

The food composition may be formulated to be administered from once to eight times daily, e.g., once to four times daily. Thus, the food composition may be formulated to an appropriate unit dosage form.

The food composition of the disclosure may be provided in the form of a powder, a gel, a solution, a suspension, a paste, a solid, a liquid, a liquid concentrate, a powder which may be reconstituted, a shake, a concentrate, a pill, a bar, a tablet, a capsule or a ready-to-use product. It is contemplated that a food composition can also be a pharmaceutical composition when it is in the form of a tablet, pill, capsule, liquid, aerosol, injectable solution, or other pharmaceutically acceptable formulation.

The disclosure further provides a process of preparing a food composition of the disclosure, wherein the amino acids may be dissolved or dispersed in water and spray dried.

The amino acids may be mixed with additional components such as macronutrients and micronutrients. Binders, emulsifiers or other ingredients suitable for human or animal consumption may be added as desired.

In another aspect, the disclosure provides a method for treating cancer in a subject in need thereof, which may comprise controlling the subject's glycine and serine intake, wherein the glycine the subject takes may account for about 0.0016-0.6 wt % of the total amino acids the subject takes, and the serine the subject takes may account for about 0.00109-1.2 wt % of the total amino acids the subject takes. The method may comprise partly or completely substituting or replacing the normal diet of the subject with the food composition of the disclosure. The method may last e.g., 12 weeks.

As mentioned above, the glycine-serine-free diet, and the glycine-serine-low diet (with a glycine-to-total amino acid ratio of 0.0016-0.6 wt % and a serine-to-total amino acid ratio of 0.00109-1.2 wt %), can increase PD-L1 molecules on tumor cell surfaces by promoting PD-L1 lactylation and synergize with the anti-PD-1 treatment.

Therefore, in another aspect, the disclosure provides a method for treating cancer in a subject thereof, which may comprise i) controlling the subject's glycine and serine intake, wherein the glycine the subject takes may account for about 0-0.6 wt % of the total amino acids the subject takes, and the serine the subject takes may account for about 0-1.2 wt % of the total amino acids the subject takes, and ii) administering the subject a therapeutically effective amount of an anti-PD-1 antibody (such as an antagonistic anti-PD-1 antibody), or an anti-PD-L1 antibody (such as an antagonistic anti-PD-L1 antibody). The method may comprise partly or completely substituting or replacing the normal diet of the subject with a food composition, wherein the amino acids or the salts thereof in the food composition may comprise about 0-0.6 wt % of glycine or the salt thereof and about 0-1.2 wt % of serine or the salt thereof.

The method may comprise partly or completely substituting or replacing the normal diet of the subject over a time period of at least 1 day, 2 days, 3 days, 4 days, 5 days, 6 days, 7 days, at least 2 weeks, 3 weeks, 4 weeks, 5 weeks, 6 weeks, 7 weeks, 8 weeks, 9 weeks, 10 weeks, 11 weeks, 12 weeks, or until a therapeutic endpoint is observed, e.g., tumor shrinkage is observed.

The cancer may be a solid tumor, including, but not limited to, colorectal cancer (e.g., pMMR/MSS colorectal cancer), esophageal cancer and nasopharyngeal cancer.

The disclosure further provides a method for sensitizing tumor cells to an anti-PD-1 or anti-PD-L1 therapy in a subject in need thereof, comprising controlling the subject's glycine and serine intake, wherein the glycine the subject takes may account for about 0-0.6 wt % of the total amino acids the subject takes, and the serine the subject takes may account for about 0-1.2 wt % of the total amino acids the subject takes. The method may comprise partly or completely substituting or replacing the normal diet of the subject with a food composition of the disclosure, wherein the amino acids or the salts thereof in the food composition may comprise about 0-0.6 wt % of glycine or the salt thereof and about 0-1.2 wt % of serine or the salt thereof.

The method may comprise partly or completely substituting or replacing the normal diet of the subject over a time period of at least 1 day, 2 days, 3 days, 4 days, 5 days, 6 days, 7 days, at least 2 weeks, 3 weeks, 4 weeks, 5 weeks, 6 weeks, 7 weeks, 8 weeks, 9 weeks, 10 weeks, 11 weeks, 12 weeks, or until a therapeutic endpoint is observed, e.g., tumor cell is sensitized.

The method may be performed before the anti-PD-1 or anti-PD-L1 therapy. Alternatively, the method and the anti-PD-1 or anti-PD-L1 therapy may be performed concurrently.

The present invention will be further illustrated in the following Examples which are given for illustration purposes only and are not intended to limit the invention in any way.

EXAMPLES

Example 1. Effect of Serine or Glycine Treatment on Tumor Cell Growth and Migration The effect of serine or glycine treatment on tumor cell growth or migration was measured in 10 tumor cell lines, including A431, MCF-7, HeLa, HepG2, PC3, SKOV3, A549, U251, K562, and Caco-2.

Briefly, $1 \times 10^4$ tumor cells were plated onto 96-well plates and cultured for 48 hours at 37° C. in 200 μl amino acid-free DMEM high glucose medium (Gibco, A14430-01) supplemented with 200 mg/L anhydrous calcium chloride, 0.1 mg/L ferric nitrate nonahydrate, 400 mg/L potassium chloride, 97.67 mg/L anhydrous magnesium chloride, 125 mg/L anhydrous $NaH_2PO_4$, 84 mg/L L-arginine hydrochloride, 84 mg/L L-cystine hydrochloride, 584 mg/L L-glutamine, 42 mg/L L-histidine hydrochloride, 105 mg/L L-isoleucine, 105 mg/L L-leucine, 146 mg/L L-lysine hydrochloride, 95 mg/L L-threonine, 16 mg/L L-tryptophan, 104 mg/L sodium tyrosine, 94 mg/L L-valine, 4 mg/L D-calcium pantothenate, 4 mg/L folic acid, 7.2 mg/L inositol, 4 mg/L niacinamide, 0.4 mg/L riboflavin, 4 mg/L ammonium chloride, 4 mg/L pyridoxine hydrochloride, 110 mg/L sodium pyruvate, and 15 mg/L phenol red, with (i) no serine or glycine (control), (ii) 0.00109, 0.2, 0.5, 1.2 or 1.5 wt % serine and 1.7 wt % glycine (based on total amino acid content), (iii) 0.0016, 0.2, 0.4, 0.6 or 0.8 wt % glycine and 2.3 wt % serine (based on total amino acid content), or (iv) 0.00109 wt % serine and 0.0016 wt % glycine, 0.2 wt % serine and 0.2 wt % glycine, 0.5 wt % serine and 0.4 wt % glycine, 1.2 wt % serine and 0.6 wt % glycine, or 1.5 wt % serine and 0.8 wt % glycine (based on total amino acid content). All non-essential amino acids were sourced from Sigma-Aldrich.

The cells were then subjected to an MTT assay and a Transwell migration assay. Each test was conducted in triplicate to ensure reproducibility.

The MTT assay was performed using a MTT kit (Beyotime, ST316) following the manufacturer's manual. The absorbance at 570 nm was measured in a microplate reader, to reflect the number of viable cells. The group with the highest OD570 value was set as the reference group, and the growth % was calculated as (OD570 of a certain group/OD570 of the reference group)×100%.

The Transwell migration assay was done with a starting cell density at $1 \times 10^5$ cells per well, using Transwell® insert (8.0 m pore size, Cat #3422) following the manufacturer's manual. The group with the highest cell count was set as the reference group, and the migration or metastasis percent was calculated as (the cell count of a certain group/the cell count of the reference group)×100%.

The results were shown in FIG. 1 to FIG. 10. It can be seen that the tumor cells cultured with either low serine level or low glycine level grew slowly but showed relatively high migration capability, as compared to the cells treated with high serine and glycine levels. The cells in the control group cultured in cell media without serine or glycine also grew slowly but showed the highest migration activity.

The data suggested that the presence of serine or glycine at relatively low levels, rather than absence of these two amino acids, can effectively suppress tumor cell growth, proliferation and migration. In other words, the presence of serine and glycine at appropriate levels may control tumor development and metastasis.

Example 2. Effect of Other Non-Essential Amino Acids on Tumor Cell Growth and Migration The effect of the other non-essential amino acids on tumor cell growth or migration was determined using CT26 tumor cells (ATCC, CRL-2638), in the absence of serine or glycine, or in the presence of different levels of serine and glycine.

Briefly, $1×10^4$ CT26 cells were seeded into 96-well plates and cultured for 48 hours at 37° C. in 200 μl amino acid-free DMEM high glucose medium (Gibco, A14430-01), supplemented with 10% amino acid-free fetal bovine serum ((Sorfa, SX1500), 1% Penicillin/Streptomycin/Amphotericin B, 4% of MEM Amino Acids Solution (Gibco, 11130036), and non-essential amino acid(s) as specified below. All the non-essential amino acids were purchased from Sigma-Aldrich.

For the cells of Group 1 (the Ctrl(+) group)), the cell culture media contained 9 non-essential amino acids at the base concentrations, i.e., 84 mg/L L-arginine hydrochloride, 2.5 mg/L L-alanine, 75 mg/L L-glutamic acid, 584 mg/L L-glutamine, 4 mg/L L-proline, 104 mg/L sodium tyrosine, 84 mg/L L-cystine hydrochloride, 2 mg/L L-aspartic acid, and 5 mg/L L-asparagine, plus a 50% increase of 1 of the 9 non-essential amino acids. For example, in the Ctrl(-)-Arginine group, the cell culture media contained 126 (84*150%) mg/L L-arginine hydrochloride, 2.5 mg/L L-alanine, 75 mg/L L-glutamic acid, 584 mg/L L-glutamine, 4 mg/L L-proline, 104 mg/L sodium tyrosine, 84 mg/L L-cystine hydrochloride, 2 mg/L L-aspartic acid, and 5 mg/L L-asparagine. No serine or glycine was added to the cells of this group.

For the cells of Group 2 (the Mid Add(+) group)), the cell culture media contained i) 1.2 wt % serine and 0.6 wt % glycine (both based on total amino acids), and ii) 9 non-essential amino acids at the base concentrations, plus a 50% increase of 1 of the 9 non-essential amino acids.

For the cells of Group 3 (the High Add(+) group)), the cell culture media contained i) 5 wt % serine and 2.5 wt % glycine (both based on total amino acids), and ii) 9 non-essential amino acids at the base concentrations, plus a 50% increase of 1 of the 9 non-essential amino acids.

For the cells of Group 4 (the Ctrl(-) group)), the cell culture media contained 8 of the 9 non-essential amino acids (i.e., arginine, L-alanine, L-glutamic acid, L-glutamine, L-proline, tyrosine, L-cystine, L-aspartic acid, and L-asparagine) at the base concentrations as described above. For example, for the cells from the Ctrl(-)-Arginine group, the cell culture medium contained the 9 non-essential amino acids except arginine, i.e., 2.5 mg/L L-alanine, 75 mg/L L-glutamic acid, 584 mg/L L-glutamine, 4 mg/L L-proline, 104 mg/L sodium tyrosine, 84 mg/L L-cystine hydrochloride, 2 mg/L L-aspartic acid, and 5 mg/L L-asparagine. No serine or glycine was added to the cells of this group.

For the cells of Group 5 (the Mid Add(-) group)), the cell culture media contained i) 1.2 wt % serine and 0.6 wt % glycine (both based on total amino acids), and ii) 8 of the 9 non-essential amino acids (i.e., arginine, L-alanine, L-glutamic acid, L-glutamine, L-proline, tyrosine, L-cystine, L-aspartic acid, and L-asparagine) at the base concentrations as described above.

For the cells of Group 6 (the High Add(-) group)), the cell culture media contained i) 5 wt % serine and 2.5 wt % glycine (both based on total amino acids), and ii) 8 of the 9 non-essential amino acids (i.e., arginine, L-alanine, L-glutamic acid, L-glutamine, L-proline, tyrosine, L-cystine, L-aspartic acid, and L-asparagine) at the base concentrations as described above.

The cells were subjected to the MTT assay and the Transwell migration assay following the protocol of Example 1. The test was done in triplicate.

Figure 11:
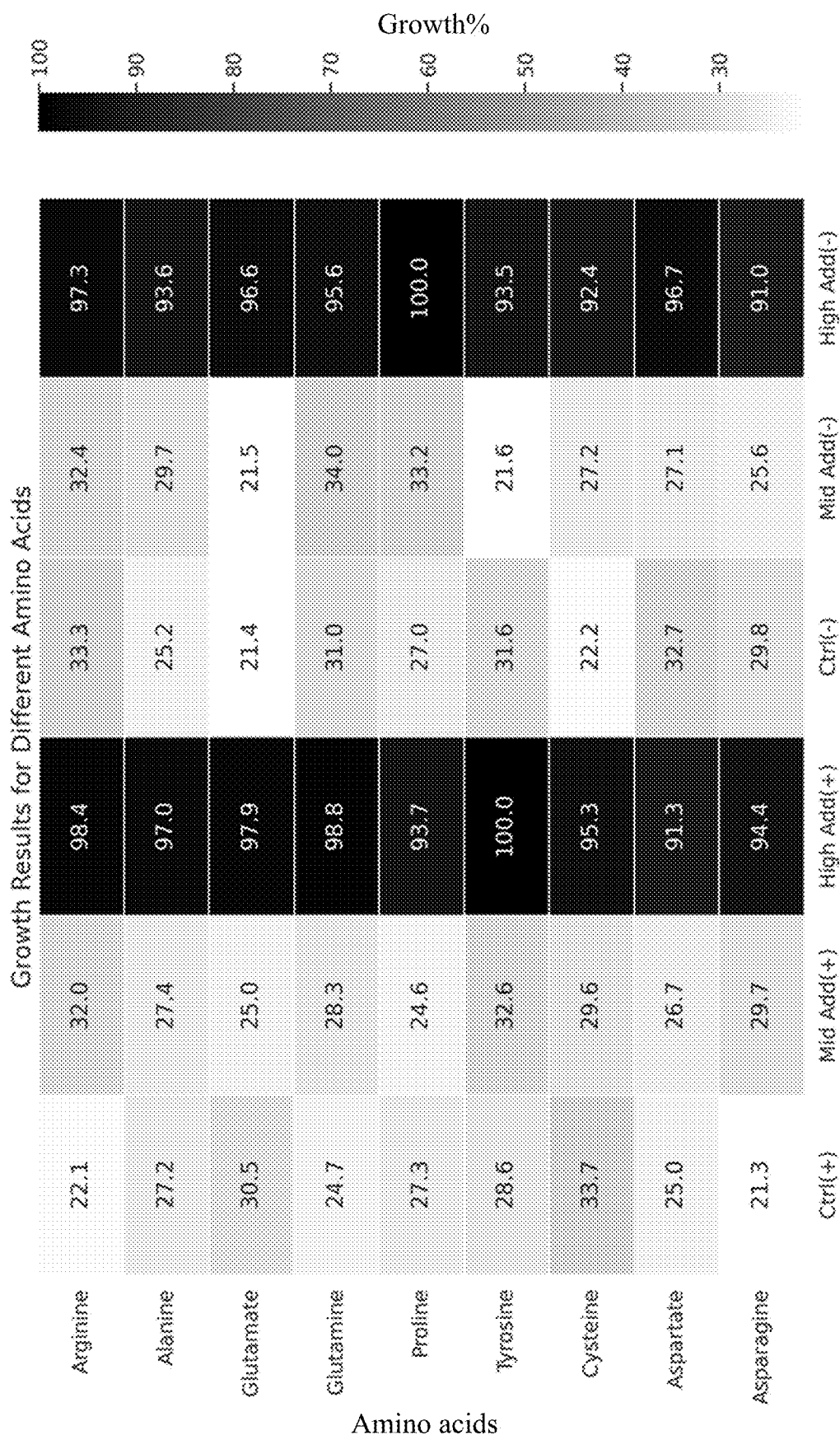
FIG. 11 shows the effect of non-essential amino acids other than glycine and serine on CT26 cell growth.
Figure 12:
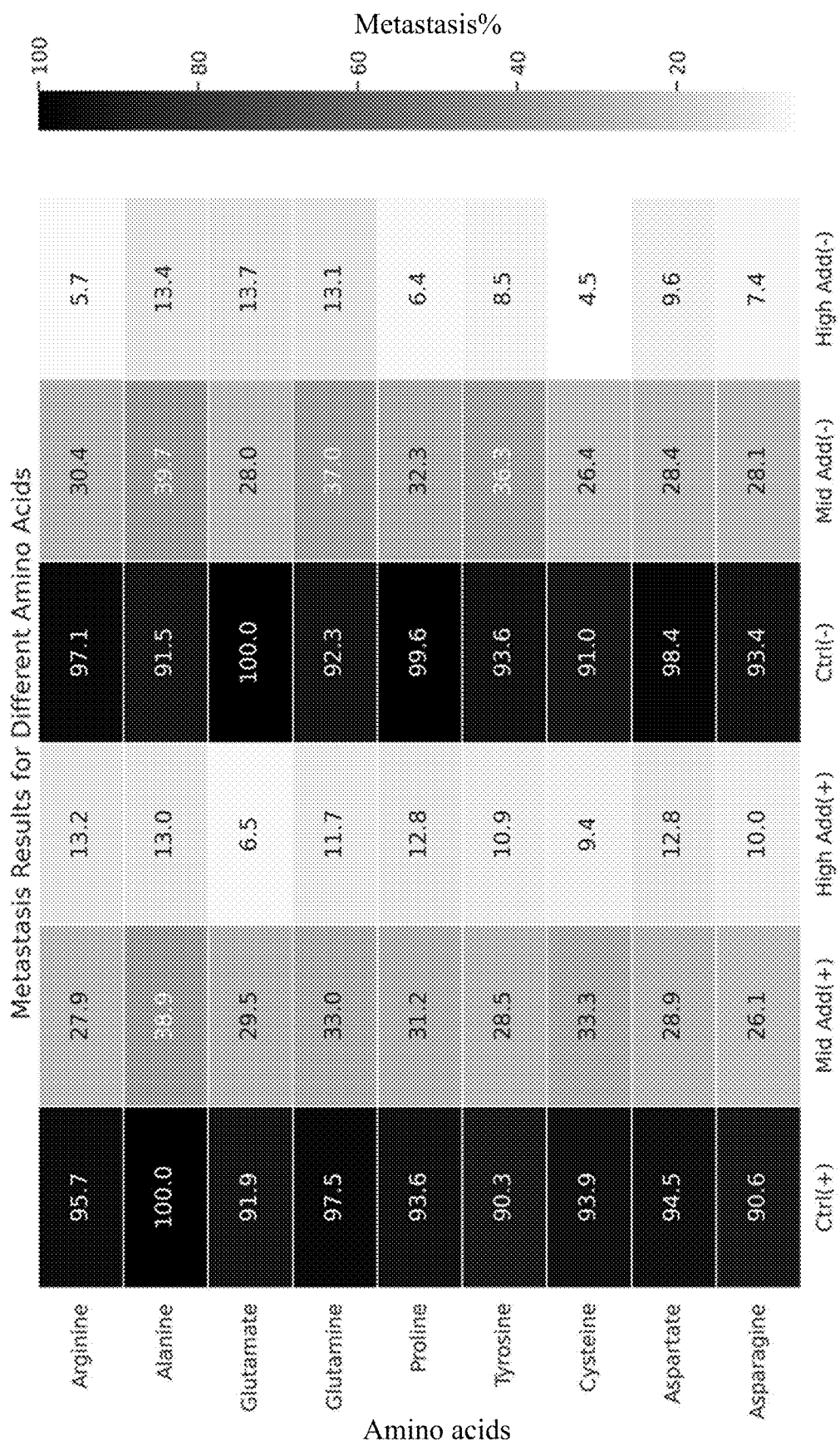
FIG. 12 shows the effect of non-essential amino acids other than glycine and serine on CT26 cell metastasis.

The results were summarized in FIG. 11 and FIG. 12.

As shown in FIG. 11, there were some tumor growth differences between the Ctrl(+) groups and the Ctrl(-) groups, between the Mid Add(+) groups and the Mid Add(-) groups, and between the High Add(+) groups and the High Add(-) groups, but tumor growth mainly depended on serine and glycine levels. The serine and glycine level increase promoted tumor growth.

As shown in FIG. 12, although there were differences between the Ctrl(+) groups and the Ctrl(-) groups, between the Mid Add(+) groups and the Mid Add(-) groups, and between the High Add(+) groups and the High Add(-) groups, tumor cell migration decreased as the serine and glycine levels increased. The cells from the Ctrl(+) and Ctrl(-) groups showed the highest migration ability, indicating ease of migration. The cells from the Mid Add(+) and Mid Add(-) groups showed lower migration ability than those from the Ctrl(+) groups and the Ctrl(-) groups but higher than those from the High Add(+) groups and the High Add(-) groups.

The data above suggested that it was serine and glycine at appropriate levels that inhibited tumor development and metastasis, the other 9 non-essential amino acids had little effect on tumor growth or metastasis.

Example 3. Anti-Tumor Efficacy of Dietary Serine and Glycine Restriction Alone or with Anti-PD-1 Treatment The inhibitory effect of serine and glycine restriction alone or with anti-PD-1 treatment on tumor growth was tested in BALB/c mice.

Briefly, male BALB/c mice, 6-8 weeks old, were allocated into 8 groups, subcutaneously injected at the right flank with $5×10^5$ CT26 cells, and began to receive feeds according to the experiment design as specified below, this day was designated as Day 0.

The mice from Group 1 (Low_PD-1) and Group 2 (Low_NO_PD-1) were fed with the feed (BioPike, LLC) containing serine and glycine respectively accounting for 0.00109% and 0.0016% of the total amino acids.

The mice from Group 3 (Moderate_PD-1) and Group 4 (Moderate_NO_PD-1) were fed with the feed containing serine and glycine respectively accounting for 0.2% and 0.2% of the total amino acids.

The mice from Group 5 (Medium_PD-1) and Group 6 (Medium_NO_PD-1) were fed with the feed containing serine and glycine respectively accounting for 1.2% and 0.6% of the total amino acids.

The mice from Group 7 (High_PD-1) and Group 8 (High_NO_PD-1) were fed with the feed containing serine and glycine respectively accounting for 1.5% and 0.8% of the total amino acids.

The mice from Group 1, Group 3, Group 5 and Group 7 were further intraperitoneally administered with 100 g anti-PD-1 antibody (Junshi Biosciences) in 100 μl PBS on Day 7, 10 and 13. The animals from Group 2, Group 4, Group 6 and Group 8 were intraperitoneally administered with 100 μl PBS as the vehicle control on Day 7, 10 and 13.

The tumor sizes of the mice were measured on Days 3, 7, 10, 12 and 13.

Figure 13:
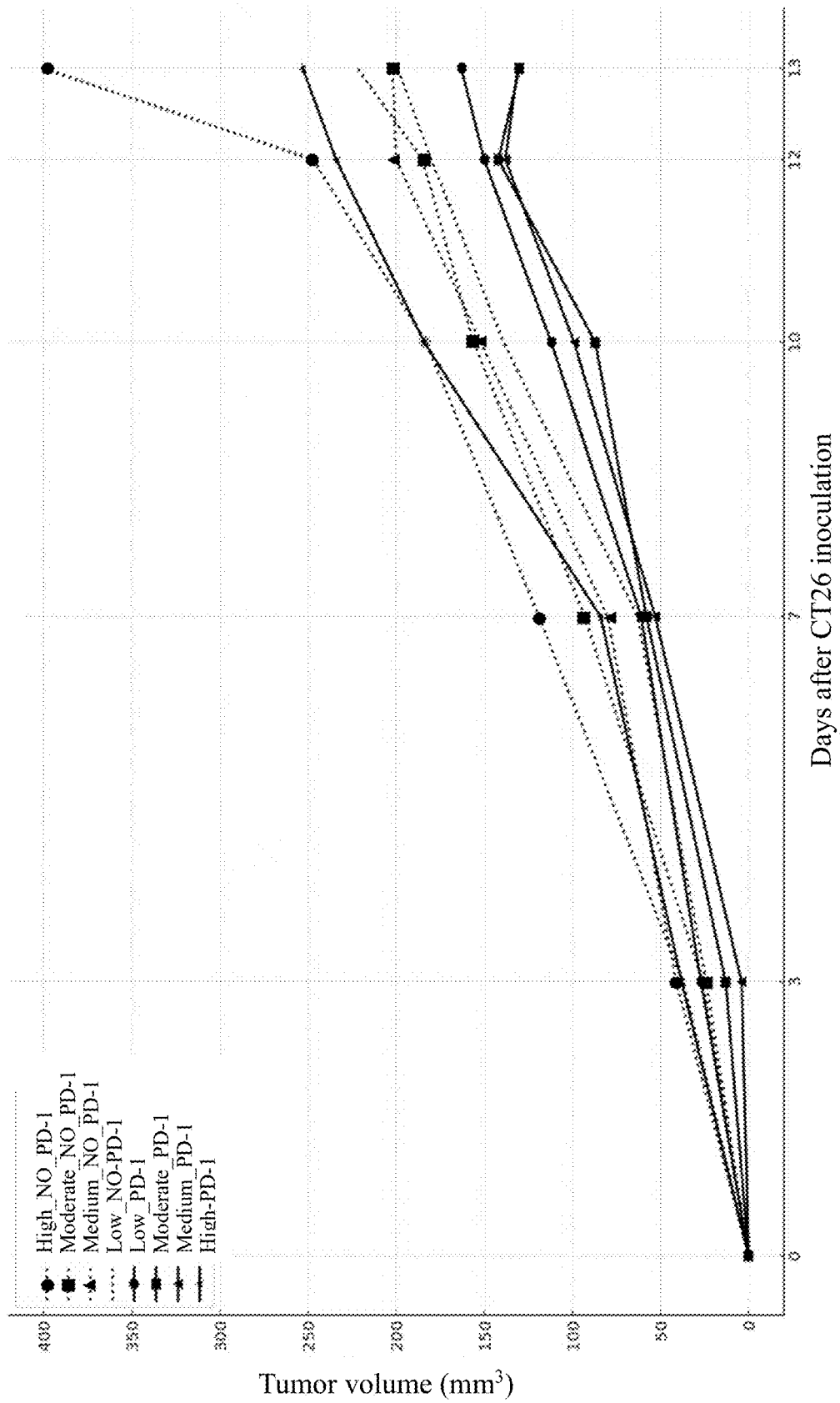
FIG. 13 shows the in vivo anti-tumor efficacy of dietary glycine and serine restriction, alone or with anti-PD-1 treatment.

As shown in FIG. 13, significant tumor suppression was observed in the mice from the Moderate_PD-1 group and the Medium_PD-1 group, followed by the mice from the Low_PD-1 group. The mice from the Moderate_NO_PD-1 group, the Medium_NO_PD-1 group and the Low_NO_PD-1 group had larger tumors than the mice from the 3 counterpart anti-PD-1+ groups, but much smaller than those from the High_NO_PD-1 and High_PD-1 groups.

The results suggested that the dietary serine and glycine restriction can significantly inhibit tumor growth, and the anti-tumor activity of such dietary restriction can be enhanced by the anti-PD-1 treatment.

Example 4. Medical Food Formula and Amino Acid Composition for Dietary Serine and Glycine Restriction Amino acid compositions with appropriate serine and glycine levels may be prepared and used to make medical food compositions for tumor patients. The medical food compositions may contain other nutrients the patients may need, including carbohydrates, proteins, and vitamins.

An exemplary medical food formula was provided below in Table 1.

TABLE 1

Exemplary medical food formula

| Item | Unit | Per 100 g |
|---|---|---|
| Energy | kJ | 1356 |
| Protein | g | 12.4 |
| Fat | g | 14 |
| Carbohydrates | g | 34.6 |
| Fiber | g | 5 |
| Sodium | mg | 385 |
| Vitamin A | μg RE | 300 |
| Vitamin $B_1$ | mg | 0.5 |
| Vitamin $B_2$ | mg | 0.7 |
| Vitamin $B_6$ | mg | 1.4 |
| Vitamin $B_{12}$ | μg | 0.785 |
| Vitamin E | mg α-TE | 18 |
| Vitamin C | mg | 142 |
| Vitamin D | μg | 3.2 |
| Niacin | mg | 1.7 |
| Folic Acid | μg | 100 |
| Zinc | mg | 3.3 |
| Calcium | mg | 280 |
| Phosphorus | mg | 155 |
| Magnesium | mg | 70 |
| Iron | mg | 4 |
| Potassium | mg | 288 |
| Copper | μg | 311 |
| Manganese | μg | 156 |
| Iodine | μg | 28 |
| Chlorine | mg | 322.4 |
| Selenium | μg | 16 |

TABLE 1-continued

Exemplary medical food formula

| Item | Unit | Per 100 g |
|---|---|---|
| Vitamin $K_1$ | μg | 24 |
| Pantothenic Acid | mg | 1.7 |
| Biotin | μg | 16 |

The protein in the above formula may have the amino acid compositions set forth in Table 2.

TABLE 2

Exemplary amino acid compositions

| Item | Composition 1 (wt %) | Composition 2 (wt %) |
|---|---|---|
| Aspartic Acid | 10.02 | 12.9 |
| Threonine | 4.5 | 5.5 |
| Serine | 0.81 | 0.5 |
| Glutamic Acid | 12.85 | 13.2 |
| Glycine | 0.41 | 0.5 |
| Alanine | 4.8 | 6.35 |
| Cystine | 1.4 | 1.47 |
| Valine | 6.1 | 6.4 |
| Methionine | 5.9 | 4.8 |
| Isoleucine | 4.63 | 5.6 |
| Leucine | 9.82 | 11.08 |
| Tyrosine | 3 | 3.4 |
| Phenylalanine | 4.2 | 4.1 |
| Histidine | 2.9 | 2.87 |
| Lysine | 5.1 | 4.35 |
| Arginine | 6.2 | 0 |
| Proline | 4.4 | 4.8 |
| Tryptophan | 3.5 | 2.07 |
| Asparagine | 4.6 | 4.01 |
| Glutamine | 4.86 | 6.1 |

An exemplary medical food composition was prepared by i) mixing compound vitamins (VR24469231, DSM Vitamin (Shanghai) Co., Ltd.), edible flavorings (Hasegawa Flavors (Suzhou) Co., Ltd.), sucralose (Anhui Jinhe Industrial Co., Ltd.), and maltodextrin (Cargill Bio-chemical Co., Ltd.) to obtain premix 1, wherein the ratio of vitamins+edible flavorings+sucralose to maltodextrin was 1:10 w/w, ii) mixing compound minerals (VR24470231, VR24471231, DSM Vitamin (Shanghai) Co., Ltd.) and maltodextrin (the same amount as in step i) or premix 1) to obtain premix 2, and iii) mixing premix 1, premix 2, Plant-derived Compound Amino Acid Powder (61B07-16B, Dalian Yunuo Biotech Co., Ltd.), pectin (Yantai Andre Pectin Co., Ltd.), and Plant Oil Micro-encapsulated Powder (40506-110, Dalian Yunuo Biotech Co., Ltd.) to obtain the final blend. The blend was then subjected to foreign substance inspection and packaging.

The medical food composition as prepared was intended to be used as a meal replacement, especially a full-day meal replacement, for certain cancer patients. The patients are recommended to take 45-80 g of the medical food composition per serving, 5-8 times per day, and to mix the composition with warm water at a powder-to-water ratio of 1:4-8 before oral consumption or tube feeding (for patients with nasogastric/intestinal tubes or gastric/intestinal fistula).

Example 5. Safety and Efficacy of Dietary Serine and Glycine Restriction in Tumor Patients Patients with solid tumors were enrolled and subjected to self-controlled dietary intervention, to test the safety and efficacy of the dietary serine and glycine restriction.

During the dietary intervention, the patients were only allowed to orally take i) the medical food composition as prepared in Example 4 with the formula of Table 1 and the amino acid composition 1, and ii) the food set forth in Table 3 containing low protein amount, along with complex vitamin and mineral tablets (Carlyle Trace Minerals, as additional supplement). The maximal daily serine intake from the food in Table 3 was 36 mg, and the maximal daily glycine intake from the food in Table 3 was 16 mg.

The research was done in West China Hospital, Sichuan University.

The inclusion criteria included:

Patients aged 18-70, gender not limited.

BMI≥18.5.

NRS-2002 scale score <3.

Diagnosed with solid tumors in stage IIIa and above.

Capable of oral intake or through gastric tube, tolerant for enteral nutrition.

Willing to participate in the study and provide written informed consent.

TABLE 3

Food for patients undergoing dietary serine and glycine restriction

| Food Name | Daily Allowance (g) | Food Name | Daily Allowance (g) |
| --- | --- | --- | --- |
| Tomato | 100 | Strawberry | 50 |
| Loofah | 100 | Orange | 75 |
| Wax gourd | 200 | Kumquat | 75 |
| Cabbage | 50 | Honey tangerine | 75 |
| Lettuce | 75 | Pomelo | 50 |
| Celery | 50 | Pineapple | 50 |
| Apple | 125 | Longan | 50 |
| Pear | 250 | Lychee | 50 |
| Peach | 100 | Mango | 75 |
| Plum | 100 | pepino melon | 100 |
| Apricot plum | 75 | Myrica rubra | 25 |
| Cherry | 50 | Loquat | 50 |
| Kyoho grape | 150 | Papaya | 50 |
| Marels grape | 125 | Muskmelon | 100 |
| Purple grape | 100 | Watermelon | 125 |
| Persimmon | 100 | | |

The exclusion criteria included:

Participating in other intervention clinical trials (including drugs, nutritional supplements, medical devices, etc.) within the first 4 weeks of screening.

Presence of severe diarrhea, intractable vomiting, severe malabsorption syndrome, paralysis, mechanical intestinal obstruction, or active gastrointestinal bleeding.

Allergy to sample components.

Taking other nutritional supplements that may affect the effectiveness of the current study.

Pregnant, lactating female patients, or those tested positive in the baseline pregnancy test.

Presence of cognitive impairments or mental illnesses, making the patients unable to comprehend the research content.

Other conditions believed to be not suitable for the current study by the researcher(s).

The exit criteria included:

Subject requesting to withdraw.

Termination of study.

Subject facing unacceptable risks.

Other circumstances requiring withdrawal.

The suspension criteria included:

Occurrence of serious adverse events during the experimental process, requiring suspension;

BMI<18.5.

NRS-2002 scale score ≥3.

Other circumstances requiring suspension.

The dietary intervention was to be terminated for a participant upon occurrence of consent withdrawal, condition worsening, severe adverse events, poor compliance, or discontinuation in the best interest of the patient in the opinion of the researchers.

After enrollment, the researchers conducted nutritional risk screening and collected basic information, blood data, imaging data, current and past medical history, and serum serine and glycine level of the participants. The participants were subjected to a 12-week dietary intervention, controlling the L-serine and L-glycine intake at 0.81% or less and 0.41% or less, respectively, based on the total food amino acids consumed. Participants were followed up every 3 weeks for a total of 4 times. Data on nutrition, blood, immunity, metabolomics, and imaging were collected during follow-ups. The serum serine and glycine levels before and after the intervention were compared.

The dietary Intervention lasted for 12 weeks. The daily protein intake for tumor patients was 1.0-1.5 g/kg/day, and energy intake was 25-30 kcal/kg/day. As indirect calorimetry was not available in this study to assess resting energy expenditure, and considering the catabolic nature of tumors requiring adequate nutrition, the study used 30 kcal/kg/day for energy and 1.5 g/kg/day for protein as standards to calculate the required food composition quantity for participants. For example, a 50 kg esophageal cancer patient with nutritional risk needed 1500 kcal and 75 g of protein per day. The medical food composition was mixed with warm water (at approximately 50° C.) at a powder-to-water ratio of 1:4-8 before oral consumption.

To ensure accurate calculation of each patient's daily appropriate amino acid intake, a food scale with a precision of 0.1 g was provided to each participant to weigh the food other than the medical food composition. The participants needed to take a photo while weighing the food, to clearly show the food and the weight displayed on the food scale.

The baseline data collected immediately after enrollment included:

① General Information: Gender, age, diagnosis, TNM staging, height, weight, educational level, marital status, family annual income, current medical history, past medical history, etc., collected by the researcher(s) through interviews with participants and reviewing patient medical records.

② Nutritional Risk: NRS2002 nutritional risk screening and PG-SGA, collected face-to-face by trained researchers using NRS2002 questionnaires and PG-SGA surveys.

③ InBody Body Composition: Including weight, body fat content, skeletal muscle content, etc.

④ Blood Indicators: Serum amino acid concentrations, liver and kidney function, myocardial enzyme spectrum, total protein amount, prealbumin level, $CD3^+$, $CD4^+$ or $CD8^+$ cell population.

⑤ Tumor Imaging: CT, MRI, or ultrasound.

⑥ Tumor Markers: CEA, CA19-9, AFP, CA125, CA153, CA724.

The items ② to ⑥ above were also collected during follow-ups. In particular, the tumor markers, the blood indicators, and nutritional risk data were collected in the $3^{rd}$, $6^{th}$, $9^{th}$ and $12^{th}$ weeks as well as the safety assessment indicators, and the tumor imaging was conducted in the 6$^{th}$ and 12$^{th}$ weeks. The safety assessment indicators included gastrointestinal adverse reactions, including the occurrence of nausea, vomiting, diarrhea, abdominal pain, etc.

Statistical analysis was conducted using SAS9.4, with paired t-tests, chi-square tests, correlation analysis, linear regression, or logistic regression, data yielding a P<0.05 was considered statistically significant.

Between March 2022 and September 2023, a total of 28 patients with advanced solid tumor were assessed for eligibility and 20 patients (with esophageal or colorectal cancer) were enrolled in the single-arm trial, among which five patients withdrew midway because they failed to adapt to the designed daily diet. All patients received PD-1 treatment (Junshi Biosciences) during the trial. Ultimately, 20 patients completed at least one cycle of the dietary restriction and were included in the statistical analysis.

The numbers of GZMB$^+$CD4$^+$ T cells and GZMB$^+$CD8$^+$ T cells, two kinds of T cells that play central role in tumor immunity, in the blood samples were determined by flow cytometry, and the proportion of GZMB$^+$CD4$^+$ T cells in CD4$^+$ cells and the proportion of GZMB$^+$CD8$^+$ T cells in CD8$^+$ cells were analyzed by Flowjo V_10.

Figure 14:
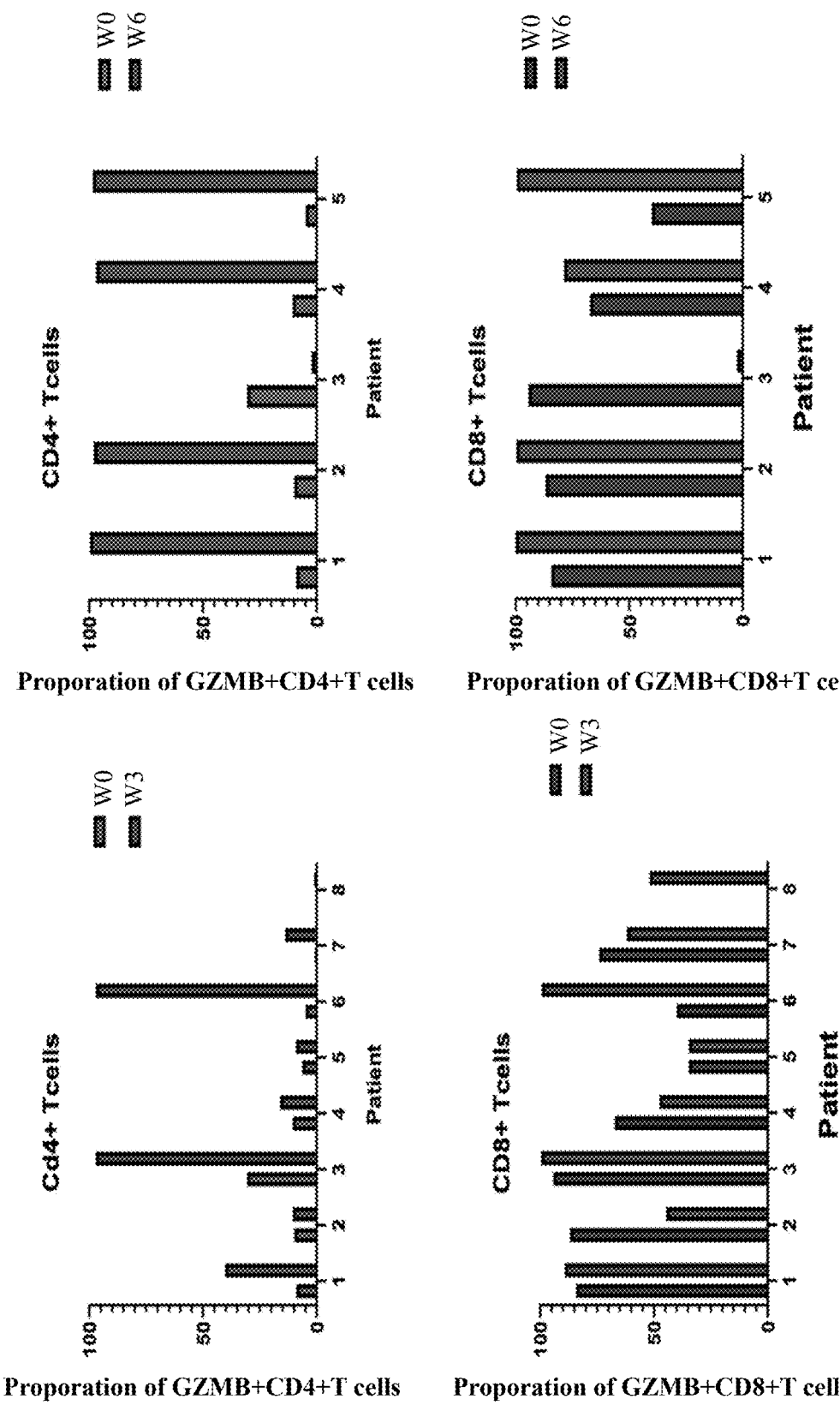
FIG. 14 shows the proportion of GZMB$^+$CD4$^+$ T cells in CD4$^+$ cells and the proportion of GZMB$^+$CD8$^+$ T cells in CD8$^+$ cells in patients before dietary glycine and serine restriction and after 3 weeks of such dietary intervention (left panels) or after 6 weeks of such dietary intervention (right panels).

FIG. 14 showed the proportions of GZMB$^+$CD4$^+$ T cells and GZMB$^+$CD8$^+$ T cells before (week 0 or W0) and after 3 or 6 weeks (W3, W6) of dietary intervention in 8 patients. A significant increase in both GZMB$^+$CD4+ and GZMB$^+$CD8$^+$ T cell levels or proportions was observed in most participants after dietary glycine and serine restriction, with the most notable increase observed in GZMB$^+$CD4$^+$ cells.

The CT results showed a reduction in tumor size in several patients.

No Grade 3 or 4 side effects were observed.

Example 6. Preparation of Exemplary Medical Food Composition for Dietary Serine and Glycine Restriction An exemplary biscuit for dietary serine and glycine restriction was prepared, containing L-glutamine (18.34%), L-leucine (10.57%), L-aspartic acid (9.30%), L-lysine hydrochloride (8.59%), L-arginine (7.18%), L-valine (5.24%), L-phenylalanine (4.36%), L-alanine (6.21%), L-proline (4.75%), L-isoleucine (5.61%), L-threonine (4.41%), L-histidine (2.23%), L-tyrosine (3.98%), L-methionine (2.62%), L-tryptophan (2.58%), L-cysteine (2.81%), L-serine (0.81%), and L-glycine (0.41%), the percent of each amino acid was based on total amino acids in the biscuit.

Briefly, 50 g softened unsalted butter (Land O Lakes Unsalted Butter, 3 pk./1 lb.) and 30 g sugar were mixed, and further added and mixed with 10 g amino acid powder (with the amino acid composition as specified above), 1/8 teaspoon of salt (for flavor balancing) and 1/2 teaspoon vanilla extract (Nielsen-Massey Madagascar Bourbon Pure Vanilla Extract). The resultant mixture was then added with 100 g cornstarch (Roots Circle 100% Pure Corn Starch 17.63 oz) gradually, stirred continuously, and added with about 20-30 ml water as needed if the mixture was too dry or difficult to form a dough. The dough was kept at 4° C. for about 30 minutes, rolled out to a thickness of about 0.5 cm, cut into desired shapes, and baked in an oven preheated to 180° C. (350° F.) for about 10-15 minutes.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

We claim:

1. A pharmaceutical composition, comprising i) a food composition, and ii) an antagonistic anti-PD-1 antibody or an antagonistic anti-PD-L1 antibody,
    wherein the food composition comprises a plurality of amino acids, wherein the plurality of amino acids comprises essential amino acids, 0.0016-0.6 wt % glycine and 0.00109-1.2 wt % serine.

2. The pharmaceutical composition of claim 1, wherein the plurality of amino acids comprises 0.2-0.6 wt % glycine and 0.2-1.2 wt % serine.

3. The pharmaceutical composition of claim 1, wherein the plurality of amino acids comprises 7 or more of 9 essential amino acids.

4. The pharmaceutical composition of claim 3, wherein the plurality of amino acids comprises the 9 essential amino acids.

5. The pharmaceutical composition of claim 1, wherein the plurality of amino acids further comprises one or more non-essential amino acids selected from the group consisting of alanine, arginine, asparagine, aspartic acid, cysteine, glutamic acid, glutamine, proline and tyrosine.

6. The pharmaceutical composition of claim 1, wherein the food composition further comprises one or more macronutrients selected from the group consisting of carbohydrates, fiber and fats.

7. The pharmaceutical composition of claim 1, wherein the food composition further comprises one or more micronutrients.

8. The pharmaceutical composition of claim 1, wherein the food composition is formulated as a solid.

9. The pharmaceutical composition of claim 1, wherein the antagonistic anti-PD-1 antibody is nivolumab or pembrolizumab.

10. The pharmaceutical composition of claim 1, wherein the antagonistic anti-PD-L1 antibody is atezolizumab, avelumab or duvalumab.

11. A method for treating cancer in a subject in need thereof, comprising:
    i) partly or completely substituting or replacing normal diet of the subject with a food composition, wherein the food composition comprises i-1) a plurality of amino acids, i-2) one or more macronutrients selected from the group consisting of carbohydrates, fiber and fats, and i-3) one or more micronutrients, wherein the plurality of amino acids comprises essential amino acids, 0.0016-0.6 wt % glycine and 0.00109-1.2 wt % serine, and
    ii) administering to the subject an antagonistic anti-PD-1 antibody or an antagonistic anti-PD-L1 antibody.

12. The method of claim 11, comprising completely substituting or replacing the normal diet of the subject with the food composition.

13. The method of claim 11, comprising partly or completely substituting or replacing the normal diet of the subject with the food composition for at least 12 weeks.

14. The method of claim 11, wherein the antagonistic anti-PD-1 antibody is nivolumab or pembrolizumab.

15. The method of claim 11, wherein the antagonistic anti-PD-L1 antibody is atezolizumab, avelumab or duvalumab.

16. The method of claim 11, wherein the plurality of amino acids comprises 0.2-0.6 wt % glycine and 0.2-1.2 wt % serine.

17. The method of claim 11, wherein the plurality of amino acids further comprises one or more non-essential amino acids selected from the group consisting of alanine, arginine, asparagine, aspartic acid, cysteine, glutamic acid, glutamine, proline and tyrosine.

18. The method of claim 11, wherein the cancer is esophageal cancer or colorectal cancer.

\* \* \* \* \*